(12) United States Patent
Taboas et al.

(10) Patent No.: US 11,583,613 B2
(45) Date of Patent: Feb. 21, 2023

(54) HYDROGEL SYSTEMS FOR SKELETAL INTERFACIAL TISSUE REGENERATION APPLIED TO EPIPHYSEAL GROWTH PLATE REPAIR

(71) Applicant: University of Pittsburgh—Of the Commonwealth System of Higher Education, Pittsburgh, PA (US)

(72) Inventors: Juan M. Taboas, Pittsburgh, PA (US); Jingming Chen, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 1121 days.

(21) Appl. No.: 16/080,220

(22) PCT Filed: Mar. 3, 2017

(86) PCT No.: PCT/US2017/020765
§ 371 (c)(1),
(2) Date: Aug. 27, 2018

(87) PCT Pub. No.: WO2017/152112
PCT Pub. Date: Sep. 8, 2017

(65) Prior Publication Data
US 2021/0205500 A1    Jul. 8, 2021

Related U.S. Application Data

(60) Provisional application No. 62/303,143, filed on Mar. 3, 2016.

(51) Int. Cl.
| | | |
|---|---|---|
| A61L 27/52 | (2006.01) | |
| A61L 27/18 | (2006.01) | |
| A61L 27/20 | (2006.01) | |
| A61L 27/22 | (2006.01) | |
| A61L 27/38 | (2006.01) | |
| A61L 27/54 | (2006.01) | |
| A61L 27/56 | (2006.01) | |

(52) U.S. Cl.
CPC .............. *A61L 27/52* (2013.01); *A61L 27/18* (2013.01); *A61L 27/20* (2013.01); *A61L 27/222* (2013.01); *A61L 27/3834* (2013.01); *A61L 27/3852* (2013.01); *A61L 27/54* (2013.01); *A61L 27/56* (2013.01); *A61L 2300/414* (2013.01); *A61L 2300/45* (2013.01); *A61L 2400/06* (2013.01); *A61L 2430/02* (2013.01)

(58) Field of Classification Search
CPC ........................ A61K 47/6903; A61K 49/0073
See application file for complete search history.

(56) References Cited

U.S. PATENT DOCUMENTS

| | | | |
|---|---|---|---|
| 6,632,457 B1 | 10/2003 | Sawhney | |
| 8,268,344 B2 | 9/2012 | Ma et al. | |
| 8,337,873 B2 | 12/2012 | Mao | |
| 9,180,166 B2 | 11/2015 | Arinzeh et al. | |
| 2007/0286880 A1* | 12/2007 | Vasiliev ............... A61L 27/3882 424/422 |
| 2011/0177134 A1 | 7/2011 | Harmon et al. | |
| 2011/0274742 A1 | 11/2011 | Arinzeh et al. | |
| 2013/0052155 A1 | 2/2013 | Marcolongo et al. | |
| 2014/0112973 A1* | 4/2014 | Steinberg ................. A61L 27/50 424/445 |
| 2014/0256843 A1* | 9/2014 | Sender ..................... A61L 27/44 523/115 |
| 2016/0095958 A1* | 4/2016 | Grayson ................. C08L 67/04 424/426 |
| 2019/0048151 A1* | 2/2019 | Wang ..................... A61L 31/148 |
| 2020/0205983 A1* | 7/2020 | Vargas Diaz ......... A61L 27/365 |
| 2021/0213170 A1* | 7/2021 | Taboas ..................... A61L 27/26 |

FOREIGN PATENT DOCUMENTS

| | | |
|---|---|---|
| WO | WO 2013/171736 | 11/2013 |
| WO | WO 2014/169236 | 10/2014 |

OTHER PUBLICATIONS

Phadke et al. (2012) Rapid self-healing hydrogels, Proc. Natl. Acad. Sci. USA, vol. 109, No. 12, pp. 4383-4388.*
Huebsch et al. (2014) Ultrasound-triggered disruption and self-healing of reversibly cross-linked hydrogels for drug delivery and enhanced chemotherapy, Proc. Natl. Acad. Sci. USA, vol. 111, No. 27, pp. 9762-9767.*
Knipe et al. (2014) Multi-responsive hydrogels for drug delivery and tissue engineering applications, Regenerat. Biomaterl. pp. 57-65.*
Yu et al. (2015) Multifunctional Hydrogel with Good Structure Integrity, Self-Healing, and Tissue-Adhesive Property Formed by Combining Diels—Alder Click Reaction and Acylhydrazone Bond, Appl. Matter., vol. 7, pp. 24023-24031.*
Sato et al. (2013) Controlled Release Strategies for Bone, Cartilage, and Osteochondral Engineering—Part I: Recapitulation of Native Tissue Healing and Variables for the Design of Delivery Systems, Tissue Eng. part B, vol. 19, No. 4, pp. 308-326.*

(Continued)

*Primary Examiner* — Suzanne M Noakes
(74) *Attorney, Agent, or Firm* — Klarquist Sparkman, LLP

(57) ABSTRACT

Described herein are biomaterials, systems, and methods for guiding regeneration of an epiphyseal growth plate or similar interfacial tissue structures. In one aspect, the disclosed technology can include a biologic material that can comprise one or more of a hydrogel carrier for growth factors and MSCs, chondrogenic and immunomodulatory cytokines, microparticles for prolonged and spatially controlled growth factor delivery; and/or porous scaffold providing mechanical support. The implanted material can be applied via various different modalities depending on the nature of the physeal injury. One modality is an injectable hydrogel and another modality is an implantable hydrogel infused scaffold.

14 Claims, 14 Drawing Sheets

(56) References Cited

OTHER PUBLICATIONS

Chau M.M. (2014) Chau (2014) Thesis "Regulation of growth plate and articular chondrocyte differentiation: implications for longitudinal bone growth and articular cartilage formation", Karolinska Institute, pp. 158.*

Nilsson et al . (2007) Gradients in bone morphogenetic protein-related gene expression across the growth plate, J. Endocrinol., vol. 193, pp. 75-84.*

Rutt J.E. (2008) Master's Thesis, Molecular analysis of the epiphyseal growth plate in rachitic broilers: evidence for the etilogy of the condition, Ohio state University, pp. 1-100.*

International Search Report and Written Opinion for related International Application No. PCT/US2019/037081, 11 pages, dated Oct. 10, 2019.

Kwon et al., "Chondroitin sulfate-based biomaterials for tissue engineering," *Turkish Journal of Biology*, 40(2):290-299 (Feb. 23, 2016).

International Search Report and Written Opinion for related International Application No. PCT/US2017/020765, dated Jun. 19, 2017, 12 pages.

Spitters et al., "A Dual Flow Bioreactor with Controlled Mechanical Stimulation for Cartilage Tissue Engineering," *Tissue Eng Part C Methods* 19.10: 774-783, 2013.

* cited by examiner

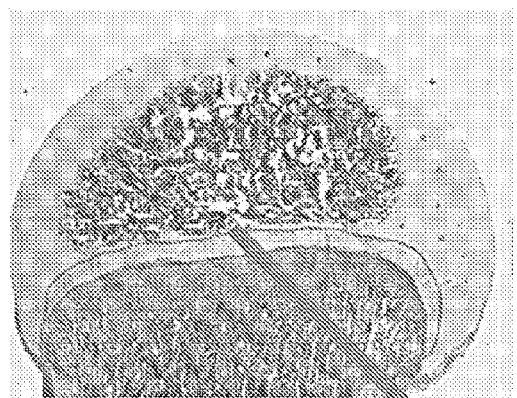
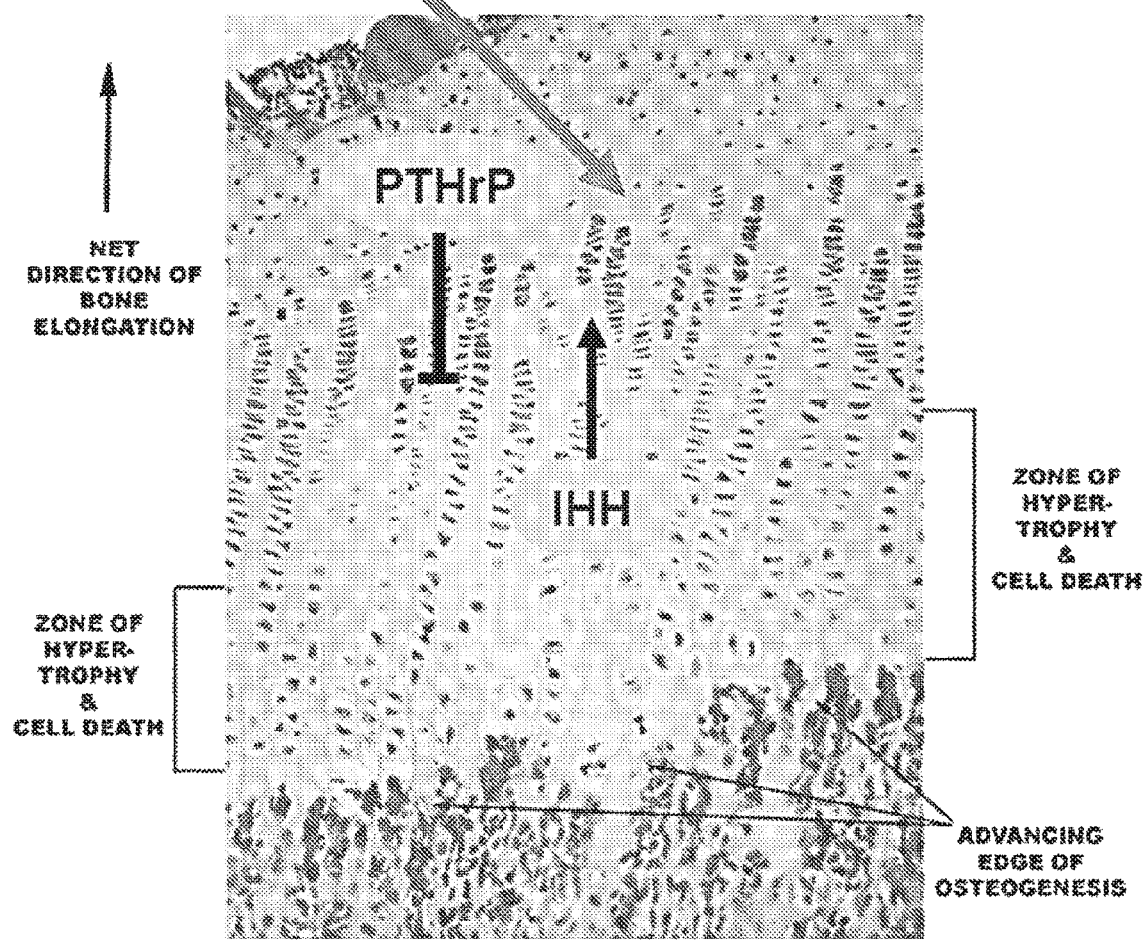
FIG. 1A

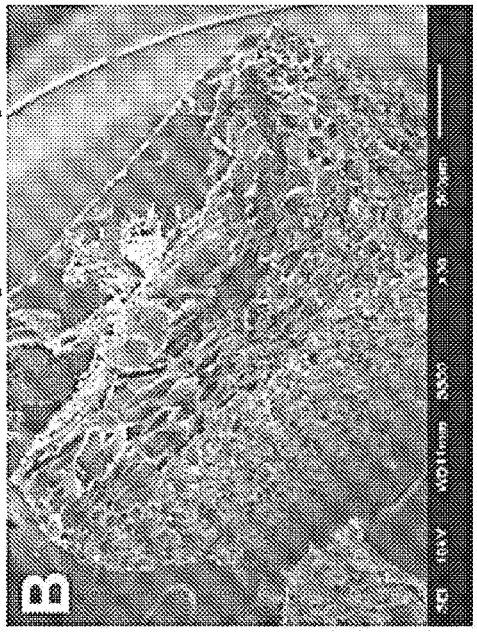
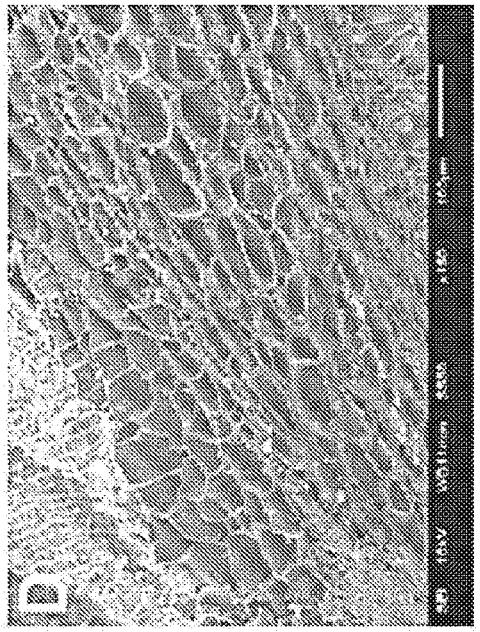
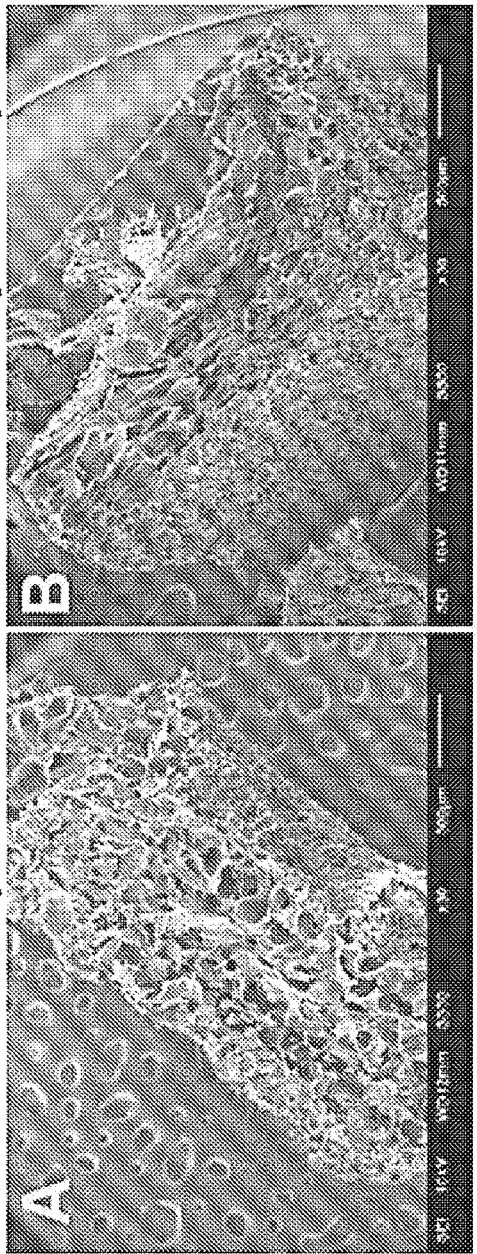
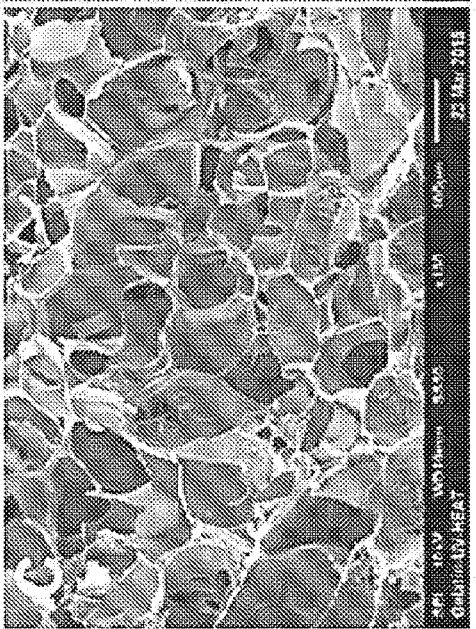
FIG. 2A Isotropic
FIG. 2B Transversely Isotropic
FIG. 2C
FIG. 2D

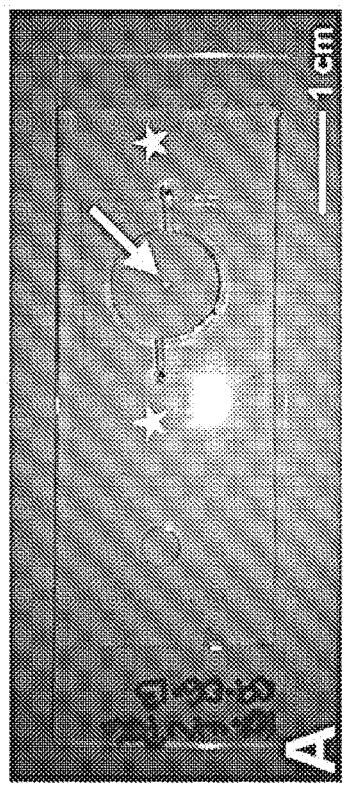
FIG. 3A
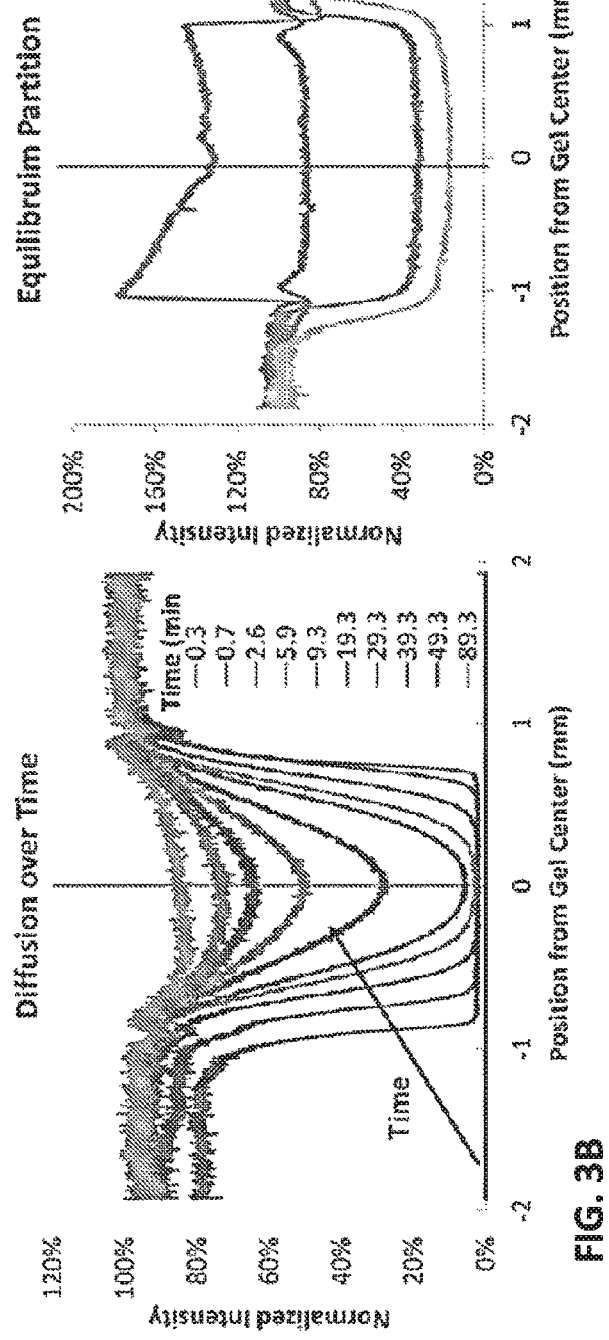
FIG. 3D
$$\frac{C(r,t)}{C_o} = 1 - \sum_{m=1}^{\infty} \frac{2}{\alpha_{m0} J_1(\alpha_{m0})} e^{-\alpha_{m0}^2 P} J_0(\alpha_{m0} L)$$
= normalized fluorescence
Equation: Analytical solution to Fick's 2nd law for radial diffusion in a cylinder.
FIG. 3B
FIG. 3C

FIG. 6A
PGH Hydrogel
FIG. 6B
GEL Hydrogel
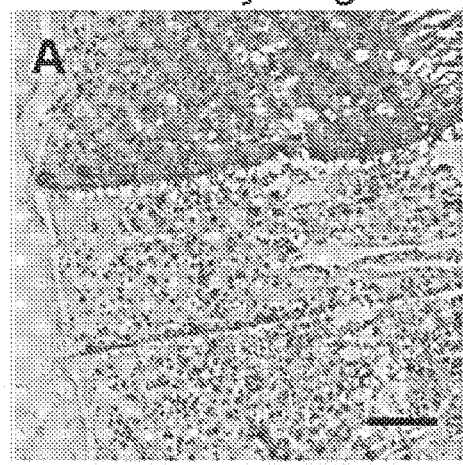
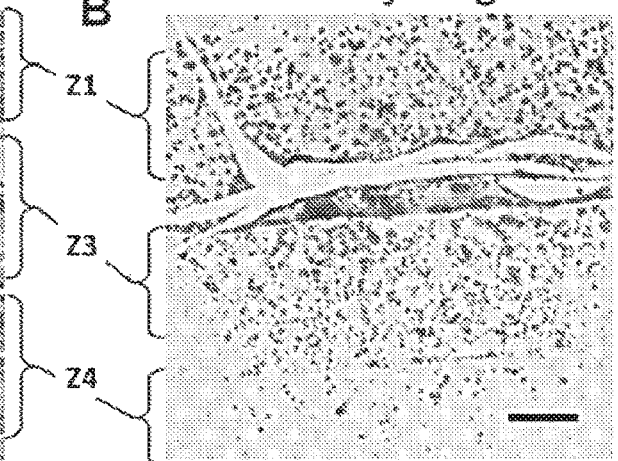
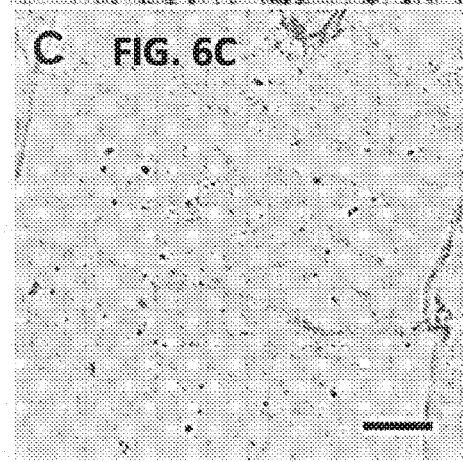
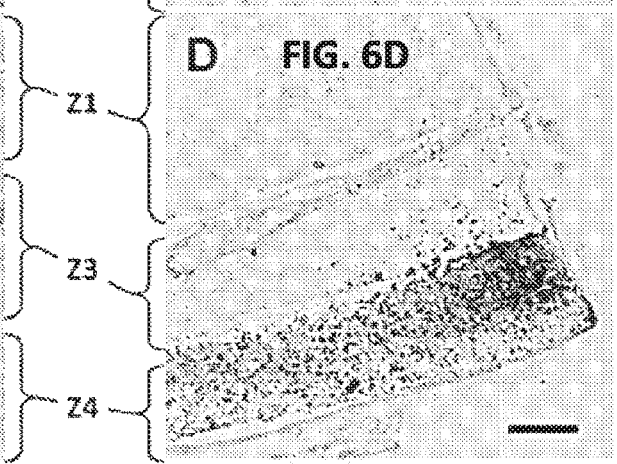
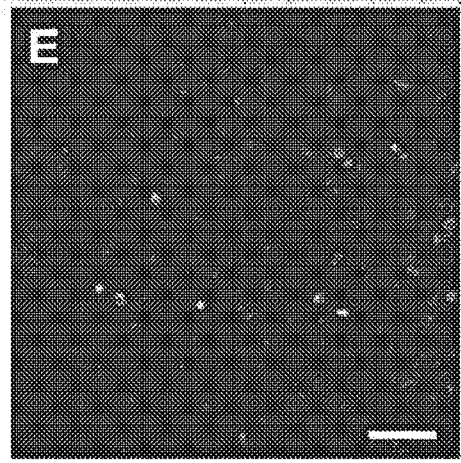
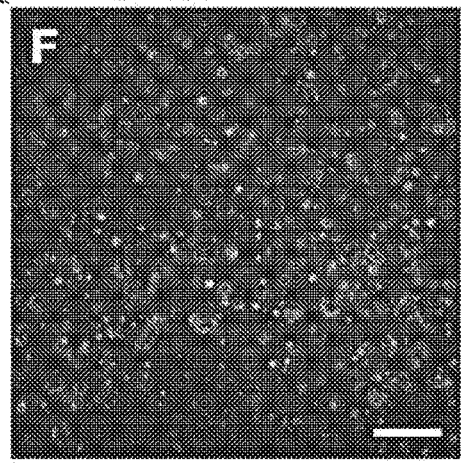
FIG. 6C
FIG. 6D
FIG. 6E
FIG. 6F

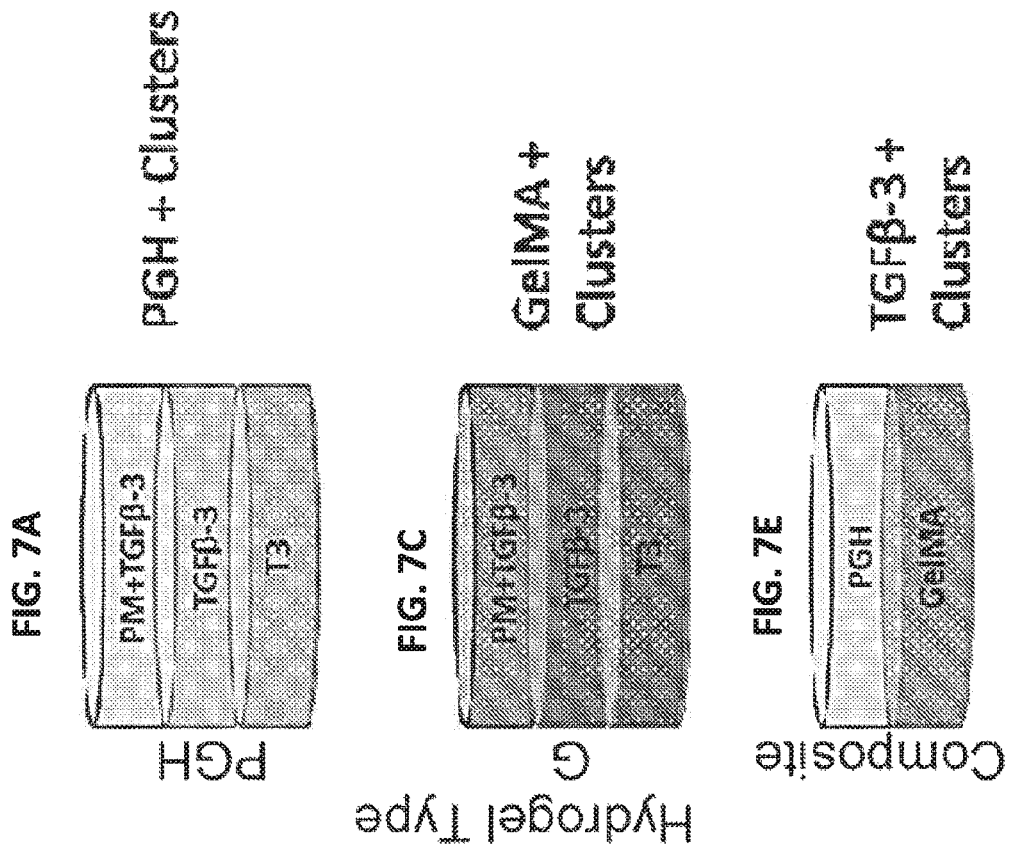

FIG. 8A
FIG. 8B
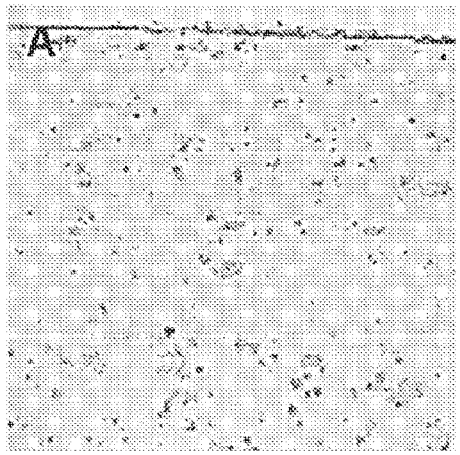
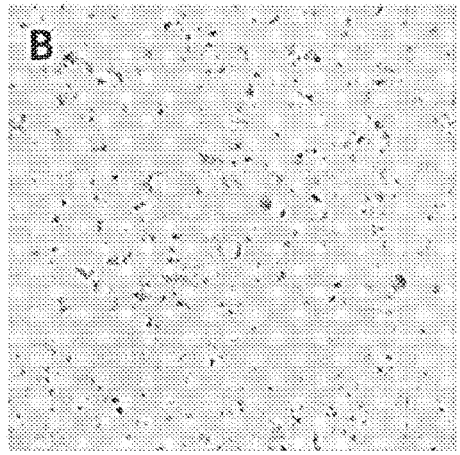
FIG. 8C
FIG. 8D
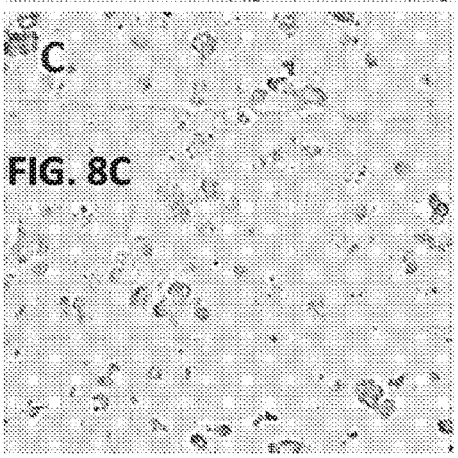
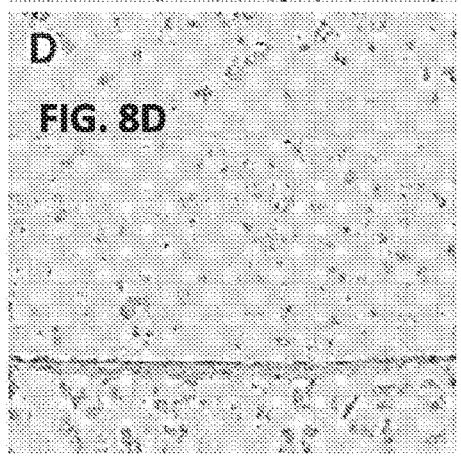
FIG. 8E
FIG. 8F
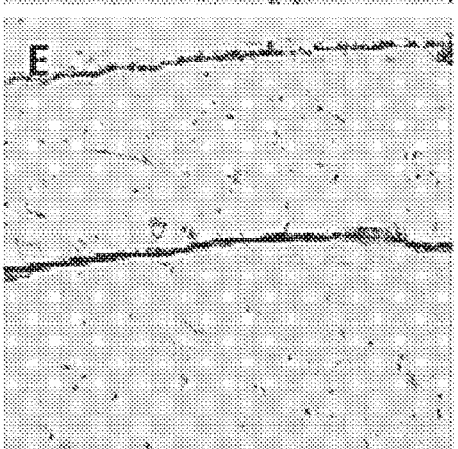
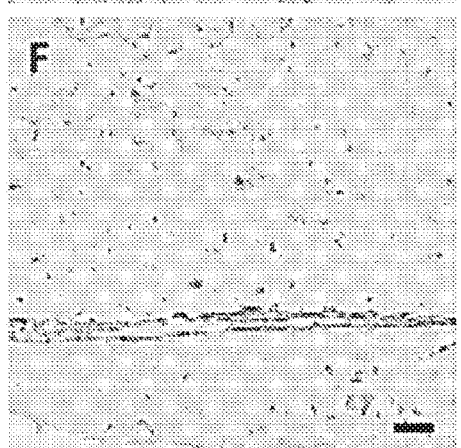

FIG. 9A
FIG. 9B
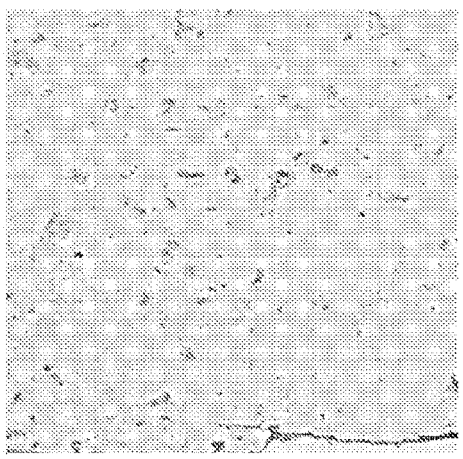
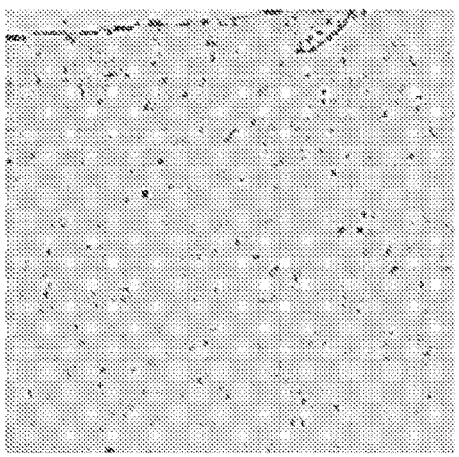
FIG. 9C
FIG. 9D
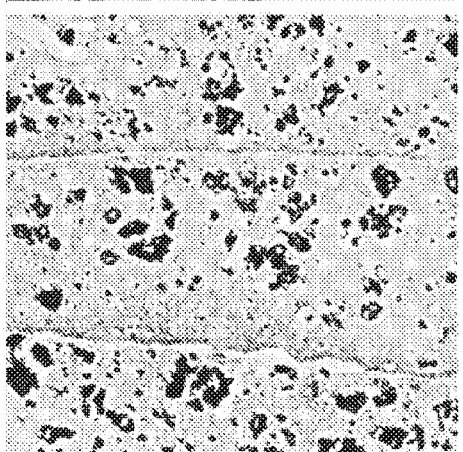
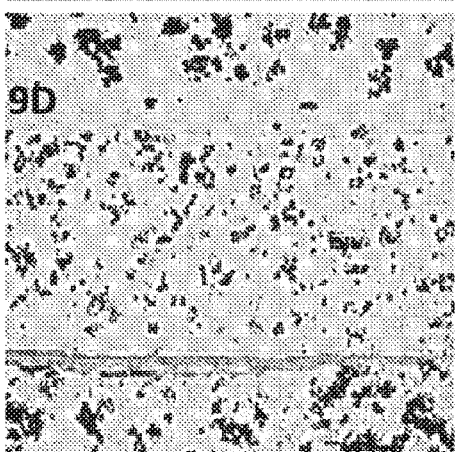
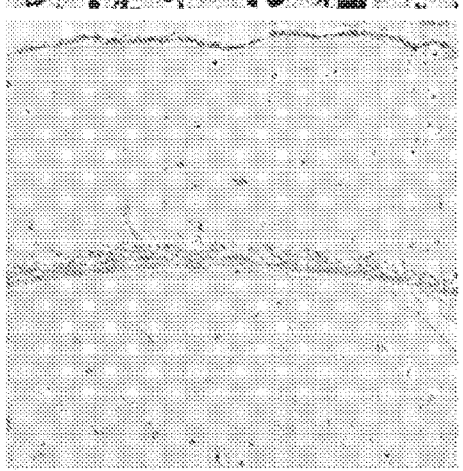
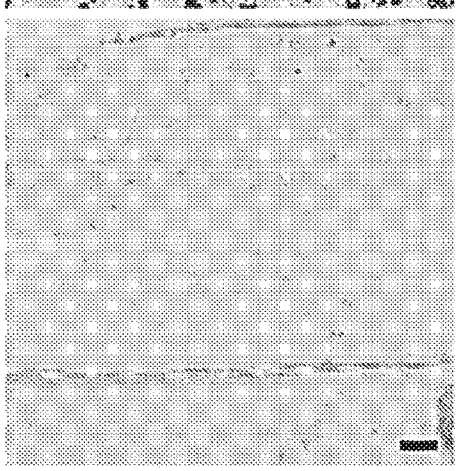
FIG. 9E
FIG. 9F

FIG. 10

FIG. 13
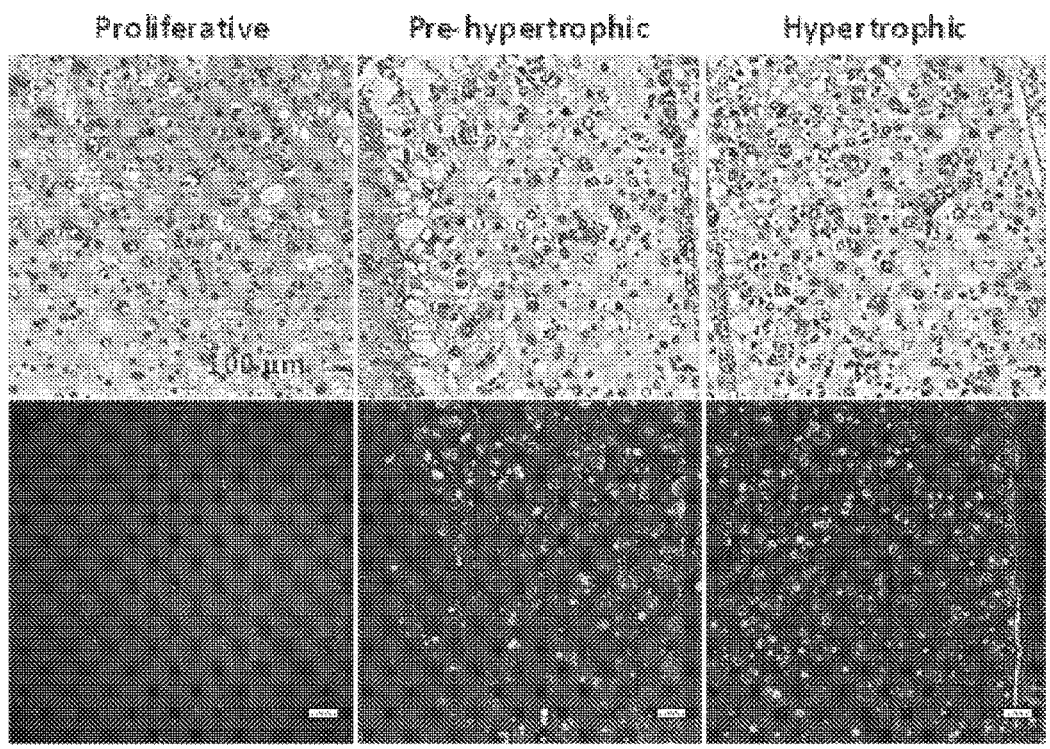
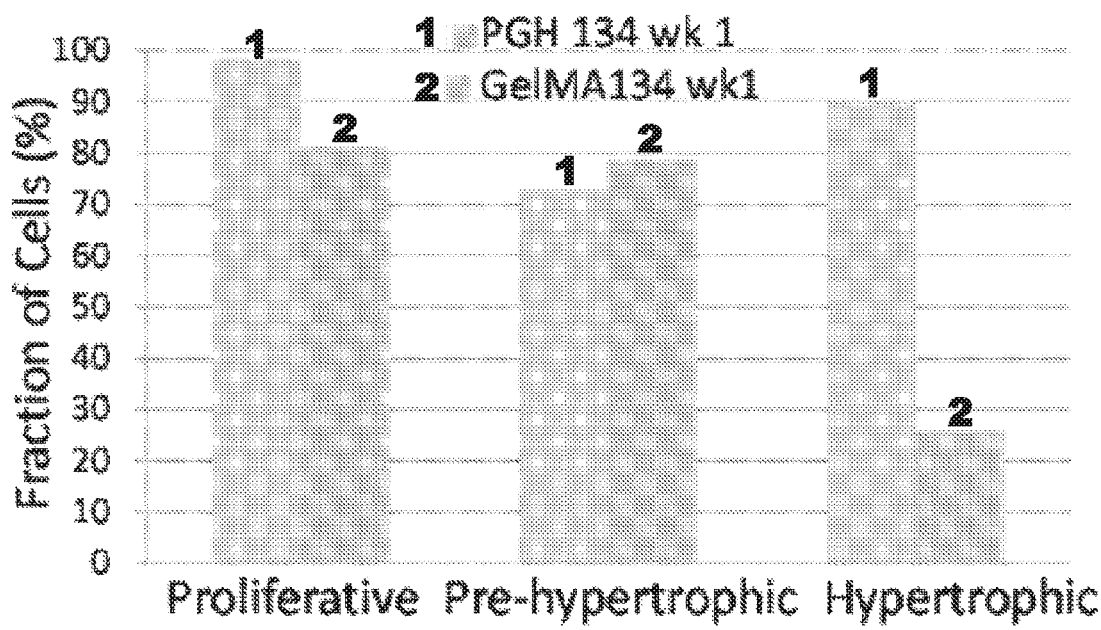
FIG. 14 Chondrogenicity After 1 Week

HYDROGEL SYSTEMS FOR SKELETAL INTERFACIAL TISSUE REGENERATION APPLIED TO EPIPHYSEAL GROWTH PLATE REPAIR

CROSS-REFERENCE TO RELATED APPLICATIONS

This application is the U.S. National Stage of International Application No. PCT/US2017/020765, filed Mar. 3, 2017, which claims the benefit of U.S. Provisional Application No. 62/303,143, filed Mar. 3, 2016, which is incorporated by reference herein in its entirety.

ACKNOWLEDGMENT OF GOVERNMENT SUPPORT

This invention was made with government support under Grant Nos. DE020740 and AR062598 awarded by the National Institutes of Health. The government has certain rights in the invention.

FIELD

This application concerns technologies for generation of skeletal interfacial tissue, especially as applied to epiphyseal growth plate repair.

BACKGROUND

Skeletal interfacial tissue structures bridge tissues that differ in mechanical properties and composition, such as the tide mark between articular cartilage and bone, the enthesis between tendon/ligament and bone, and the epiphyseal plate between epiphyseal and metaphyseal bones. The lack of proper interfacial tissue formation after tissue grafting (e.g., ACL allograft) is a critical point of failure in current orthopaedic procedures. Many regenerative medicine approaches require control over formation of interfacial tissues to bond neotissue to existing structures (e.g., neocartilage to bone for joint resurfacing) and to promote normal function (e.g., limb growth, mechanical strength). For illustrative purposes, this disclosure focuses on regeneration of the epiphyseal plate in children affected by sarcoma resection, fracture, and disease; however this is just one particular non-limiting implementation of the disclosed technology, which can also be implemented for regeneration of various other skeletal interfacial tissues, in patients of any ages, and to treat various other injuries or diseases affecting the musculoskeletal tissues.

Epiphyseal injury, due to fracture, cancer, and infection, is a significant pediatric orthopaedic problem and results in tremendous morbidity. The epiphyseal plate, or growth plate, is the cartilaginous structure at the ends of long bones that drives appendicular skeleton growth via the process of endochondral ossification. In the pediatric population, the incidence of bone fractures that involve the epiphyseal plate is high at 2.4 to 4.6 per 1,000 (about 178,800-342,700 estimated US cases for 2015). Up to 75% of these fractures cause some growth disturbance, which can lead to substantial physical impairment due to limb deformity and limb length discrepancy. The amount of growth disturbance is proportional to fracture severity, with those that traverse the epiphyseal plate typically resulting in aberrant limb growth due to formation of boney tethers that cross through the growth plate and bridge bone ends. Small growth disturbances may resolve over time, but are not well tolerated in the lower limbs. Thus corrective surgery is more common in the portion of cases with lower limb involvement. For example in knee injuries, the number of distal femoral physeal fractures estimated to have required surgical correction in 2015 is 3000 to 6000. While 30-fold more individuals are estimated to have been diagnosed with knee osteoarthritis in the same year, children live with these disorders much longer and through their most active, socially formative and productive years. To restore limb length, patients are treated with distraction osteogenesis, a long (3-6 months) and painful procedure employing hardware that pierces the skin.

Cancer-related injury is less common, but the morbidity is even greater, 5% of malignant tumors in children less than 15 years of age are osteosarcomas, with 640 cases estimated in 2015, 75% of these form near the epiphyseal plate. At least 20% of osteosarcoma cases require limb amputation because resection damage to the physis is severe and surgical reconstruction cannot restore normal growth. Surgeons attempt reconstructive techniques, such as vascularized physeal transfer from the distal limb, and perform rotationplasty to provide greater prosthesis function. There are no accepted treatments to restore epiphyseal plate function after tissue resection. Children can suffer from deformity, limb loss, functional impairment, prolonged immobilization, multiple surgeries, and/or physical and emotional pain during treatment. Costs are significant with repeated clinic visits, surgeries, rehabilitation, prosthetic maintenance, and lost future productivity.

No regenerative approach exists to prevent growth arrest after physeal injury or to repair large physeal defects and restore growth. Current clinical approaches to treat boney tether formation in the growth plate involve excision of the tether and placement of an interpositional material to prevent re-bridging. For example, the Langenskiöld procedure is one approach that fills the defect with autologous fat. However, the success rate is only 15-38% for inhibiting tether re-formation. Experimental attempts to prevent tethers using other inter-positional materials, including autologous articular cartilage and physeal allografts, have failed to promote normal growth in animal models. Investigators have studied the regenerative potential of various biomaterials and cells implanted into epiphyseal plate defects in animal models. Cell-treated limbs still show growth disruption, but with less tethering and angular deformity compared to defects with cell-free implants. Transplants of entire physes have fared better in animals, likely because they possess the organized cellular architecture that drives physeal growth. However none have been able to completely prevent growth arrest, including transplantation of epiphyseal plate derived cells. Past approaches have likely failed because they were unsuccessful in re-establishing the natural architecture of the epiphyseal plate.

No reported study has endeavored to guide cells to reestablish the zonal architecture of the epiphyseal plate to facilitate repair. The epiphyseal plate consists of chondrocytes (cartilage cells) that are spatially stratified in zones of distinct differentiation states (FIG. 1). Intercellular signaling between zones by diffusible growth factors, or morphogens, helps maintain equilibrium and drive appendicular growth. Loss of equilibrium can result in growth termination or dwarfism. Transport of parathyroid hormone (PTH) related peptide (PTHrP) and Indian hedge hog (IHH) between zones establishes a negative feedback gradient loop that regulates chondrocyte phenotype progression, zonal equilibrium and growth. Proper transport and binding of PTHrP and IHH through the ECM are important for establishing gradient profiles. Thus, biomaterials employed for growth plate regeneration can facilitate reconstitution of gradients in soluble growth factors to promote physeal architecture formation.

SUMMARY

Described herein are biomaterials, systems, and methods for guiding regeneration of a growth plate or similar interfacial tissue structures. In one aspect, the disclosed technology can include a biologic material/device that can be loaded with minimally manipulated autologous mesenchymal stem cells (MSCs) at the point-of-care.

The implanted material can comprise one or more of the following components: (1) hydrogel carrier for growth factors and MSCs; (2) chondrogenic and immunomodulatory cytokines; (3) microparticles for prolonged and spatially controlled growth factor delivery; and (4) porous scaffold providing mechanical support. The implanted material can be applied via various different modalities depending on the nature of the physeal injury. One modality is an injectable hydrogel comprising components 1, 2, and 3 above. Another modality is an implantable hydrogel infused scaffold comprising components 1, 2, 3 and 4 above.

An injectable hydrogel can be used to treat physeal fractures and small deficits after boney tether removal, for example, and the implantable hydrogel infused scaffold can be used to treat large deficits such as those resulting from osteosarcoma resection, for example (these exemplary uses are non-limiting). The hydrogels can be physically or chemically crosslinkable (solidified) via photopolymerization, via non-photo chemical bonding (e.g., thiol-ene/thiol-Michael addition), and/or via physical reactions (e.g., hydrophilic-hydrophobic interaction). Examples of physically formed hydrogel materials include PIPAAm and poloxomer materials.

In one particular example, constructs were assembled ex vivo with MSCs and components 1, and 2 above, they were implanted in subcutaneous pockets in mice (orthotropic site, not the growth plate), and evaluation of chondrogenesis, cartilage growth, and chondrocyte phenotype progression were performed. It was found that disclosed hydrogel compositions can regulate chondrogenesis by MSCs (or other stem cells) and the progression of chondrocyte differentiation to terminal hypertrophy. One exemplary hydrogel formulation (containing poly(ethylene glycol), gelatin, and heparin) can inhibit osteogenesis (differentiation into bone cells) while promoting chondrogenesis of MSCs (FIG. 8). Another exemplary formulation comprising gelatin promotes terminal hypertrophy of chondrocytes. These hydrogels, for example, can address the lack of control over MSC chondrogenesis and provide control over progression of chondrocyte phenotype.

Injectable hydrogels can be more readily translated to surgical use in patients compared to implantable scaffolds. However, it can be difficult to control the architecture of tissue formation because injectable hydrogels do not provide spatial cues to induce different cellular phenotypes and functions. Thus, testing of disclosed hydrogel biomaterials and regeneration approaches was initially conducted using a layered assembly of different materials to fabricate the implantable scaffolds with different cells, matrix composition, and growth factors throughout the construct to facilitate spatial control over cellular function. In other embodiments, self-segregating microparticles can be used that can localize to opposing regions of a defect after hydrogel injection (such as via variation in density relative to the hydrogel medium). Self-segregating microparticles can be used to deliver cells, growth factors, or drugs to discrete regions, and thereby localize different cell types or establish exogenous gradients in factors that guide formation of an appropriate cellular architecture. Self-segregating microparticles can address the problem of spatial control over cell and drug delivery in injectable formulations.

The disclosed technologies includes several independently novel and useful aspects. For example, the disclosed approach to growth plate repair is unique as there are no other effective approaches to prevent tether reformation after excision or to repair large epiphyseal defects and restore growth. Some disclosed approaches are innovative at least because they employ injectable biomaterials with microparticles that can self-sort to discrete regions of the defect site and thereby provide spatially controlled delivery of cells, growth factors, and/or drugs to guide proper tissue architecture formation. This can be used to re-create gradients of key morphogens which regulate chondrocyte differentiation through the epiphyseal plate zonal states. Implantable constructs can also be fabricated where cells, materials, and/or growth factors are patterned into spatial regions using layered assembly. In some approaches, hydrogels of different densities can be layered in situ (e.g., by injection) and then gelled simultaneously.

Furthermore, disclosed materials can, by nature of their composition:

1) control chondrogenesis by progenitor cells (e.g. mesenchymal stem cells);

2) control progression of chondrocyte phenotype (e.g. from proliferation and matrix synthesis to terminal hypertrophy and matrix mineralization):

3) retain/deliver growth factors and drugs; and/or 4) support formation of gradients of key morphogens which regulate progression of chondrocyte phenotype through the epiphyseal plate zonal states, specifically, re-creating the signaling of spatial gradients in PTHrP and IHH.

Alternative hydrogel formulations can be made using components in the same chemical families as described herein (e.g. other polysaccharides instead of heparin). However, disclosed hydrogel compositions, such as those containing poly(ethylene glycol), gelatin, and heparin, for example, have not been disclosed. In addition, applications or embodiments of disclosed hydrogel compositions are novel. For example, the ability of one formulation to promote chondrogenesis and inhibit osteogenesis by MSCs is novel. This ability alone is not only useful for growth plate repair, but can also be useful regeneration of articular cartilage and treatment of arthritis.

Furthermore, disclosed self-segregating microparticles are unique and have numerous applications in drug delivery, tissue engineering, and/or regenerative medicine.

The disclose technology can be used to repair many different skeletal interfacial tissues. These tissue structures bridge tissues that differ in mechanical properties and composition, such as the tide mark between articular cartilage and bone, the enthesis between tendon/ligament and bone, the tendinous junction between muscle and tendons, and the epiphyseal plate between epiphyseal and metaphyseal bones. Regeneration of these interfacial tissues can be needed to promote mechanical stability of tendon, ligament, and muscle transplants. The disclosed technology may also be applied to engineer other tissues with complex spatial architectures of cellular phenotypes, such as liver. Disclosed technology for generating and controlling spatial gradients of specific morphogens in 3D cell-laden hydrogels can also be useful to create microtissues for scientific study, such as in epiphyseal plate biology, where the biofactors that drive chondrocyte organization into columns and orientation of their cytoskeleton remain unclear.

The foregoing and other objects, features, and advantages of the disclosed technology will become more apparent from the following detailed description, which proceeds with reference to the accompanying figures.

BRIEF DESCRIPTION OF THE DRAWINGS

FIG. 1A shows an exemplary growth plate architecture, which includes cartilage cells that are spatially stratified in zones of distinct differentiation states, from reserve cells (top) to proliferative cells stacked in columns to hypertrophic cells (enlarged, bottom) that mineralize the matrix. Secretion and diffusion of PTHrP and IHH from distinct zones establish a negative feedback signaling axis that regulates chondrocyte progression through these states and that is essential for growth. Tissue engineering scaffolds and regenerative approaches can establish such appropriate signaling to promote normal growth.

FIGS. 2A-2D show exemplary freeze-casting and thermal crosslinking of composite hydrogels used to manufacture solid scaffolds with controlled porosity. The pores can be made to have a preferred orientation to guide blood vessel ingrowth from the periphery by controlling the ice crystal growth. Porous sheet made from PG hydrogel showing average 100 μm pores with no preferred orientation (A,C) and out-of-plane orientation (B,D). Bar=500 μm (A,C) and 100 μm (C,D).

FIGS. 3A-3D illustrate a permeability analysis system. (A) Millifluidic device with control well (left) and permeability chamber (>300 μl, right) containing 1.0 mm high×2.0 mm diameter cylindrical 10% (w/v) P hydrogel in center (3 μl volume, arrow). Stars=access ports. (B) Diffusion of Dex3 at 25 nM into cylinder. Valleys in plots at cylinder walls are produced by diffraction (immersion flow from right to left). (C) Partitioning of four surrogate morphogens in PEG cylinders. Partition coefficient is <1 for the Dexs (Dextrans), decreasing with increasing molecular weight (Dex3=3 kDa at 160 nM concentration, Dex10=10 kDa at 25 nM concentration, Dex70=70 kDa at 10 pM concentration). The coefficient is >1 for sulforhodamine (SFR), which did not reach equilibrium even at 80 μM. (D) Equation representing analytical solution to Fick's $2^{nd}$ law for radial diffusion in a cylinder.

FIGS. 6A-6F illustrate how hydrogel composition controls chondrogenesis and endochondral ossification of subcutaneous implants in mice. (A-D) Multiplex assay at 3 weeks testing chondrocytes at 3 differentiation states: Z1=proliferative, Z2=prehypertrophic, Z3=hypertrophic. (A,B) PGH hydrogel (A) promotes more cartilage matrix secretion than G hydrogel (B) shown by red glycosaminoglycan stain (red=Safranin O, green=Fast Green for fibrous tissue, purple=Hematoxylin for cell nucleus). (C,D) PGH hydrogel (C) shows delayed mineralization by hypertrophic chondrocytes compared to G hydrogel (D) shown by no black stain, the difference most apparent at 3 weeks (black=Von Kossa, pink=Eosin). (E,F) Multiplex assay at 1 week. PGH hydrogel (E) showed delayed terminal differentiation of prehypertrophic chondrocytes compared to G hydrogel (F) shown by less green immunostaining for Collagen Type 10_1 (blue=DAPI). Thus the G component promotes hypertrophy and mineralization of chondrocytes. Black bar=0.5 mm, white bar=0.2 mm.

FIGS. 7A-7F illustrate an experimental design for subcutaneous testing of hydrogel formulation effects on chondrogenesis by MSCs and on progression of chondrocyte phenotype.

FIGS. 8A-8F illustrate how hydrogel composition controls chondrogenic differentiation of human bone marrow derived stem cells (hMSCs) in subcutaneous implant (mice) loaded with the osteochondrogenic factor TGF-β3. (A-F) Histology at 8 weeks (red=Safranin O for glycosaminoglycans, green=Fast Green for fibrous tissue, purple=Hematoxylin for cell nucleus). (A,B) PGH hydrogel maintains the "stemness" of hMSCs longer and shows no fibrous or osteoblastic differentiation, only chondrogenic staining (red). No difference observed between clustered hMSCs (A) and dispersed hMSCs (B). (C,D) G hydrogels support hMSC chondrogenesis and osteogenesis shown by red stain and green stain, respectively, in both clustered (C) and dispersed (D) hMSCs. (E,F) Pre-cultured (1 week in vitro static culture) PGH and G hydrogels experienced tremendous cell loss. No significant matrix formation was observed. Black bar=0.1 mm.

FIGS. 9A-9F illustrate how hydrogel composition controls osteogenic differentiation and mineralization of hMSCs within subcutaneous implants (mice) loaded with the chondrogenic factor TGF-β3. (A-F) Von Kossa at 8 weeks (black: mineral, red: fast red counterstain). (A,B) PGH hydrogel prevents mineralization in both clustered (A) and dispersed (B) hMSCs. (C,D) G hydrogels promotes mineralization in both clustered (C) and dispersed (D) hMSCs. (E,F) No mineralization was observed in pre-cultured (1 week in vitro static culture) PGH and G hydrogels (note pre-cultured constructs showed significant cell loss. Black bar=0.1 mm.

FIG. 10 illustrates a large model animal test using a disclosed injectable composition for epiphyseal growth plate regeneration. A 3.2 mm diameter×15 mm deep defect was drilled in the proximal tibial growth plate and filled with the injectable hydrogel groups depicted. K-wires were implanted to monitor growth over time using x-ray imaging.

FIG. 13 illustrates how hydrogel compositions control chondrogenesis and endochondral ossification, for proliferative, pre-hypertrophic, and hypertrophic examples.

FIG. 14 is a graph illustrating chondrogenicity after one week as a fraction of cells, for proliferative, pre-hypertrophic, and hypertrophic examples.

DETAILED DESCRIPTION

Described herein are biomaterials, systems, and methods for guiding regeneration of a growth plate or similar interfacial tissue structures. In one aspect, the disclosed technology can include a biologic material/device that can be loaded with minimally manipulated autologous mesenchymal stem cells (MSCs) at the point-of-care. The implanted material can comprise one or more of the following components, and optionally other components:

1) hydrogel carrier for growth factors and MSCs;
2) chondrogenic and immunomodulatory cytokines;
3) microparticles for prolonged and spatially controlled growth factor delivery; and
4) porous scaffold providing mechanical support.

Figure 1B:
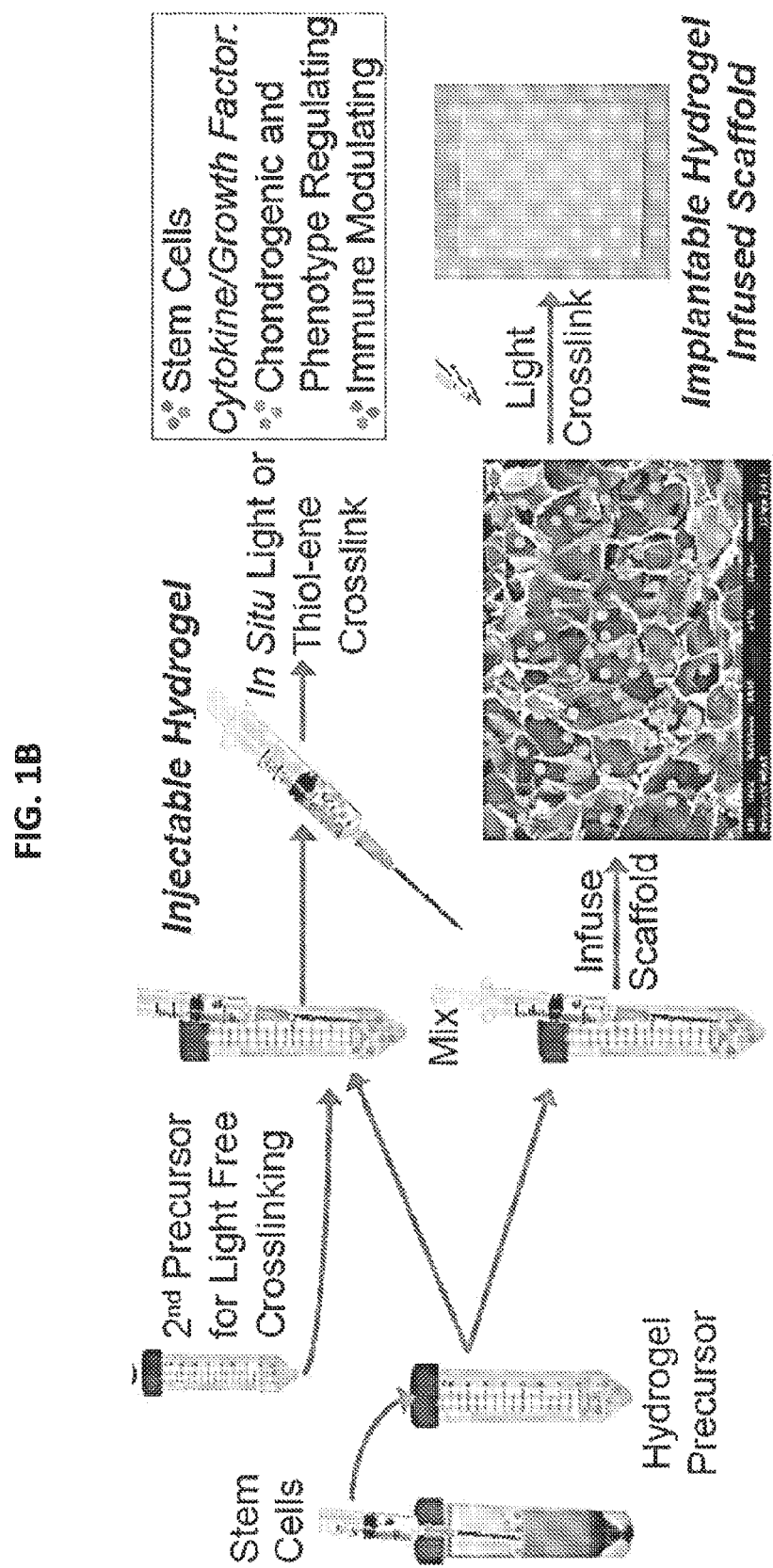
FIG. 1B illustrates point-of-care therapies for epiphyseal growth plate regeneration. Hydrogel precursors loaded with chondrogenic growth factors and immune modulating cytokines are mixed with cells and either injected into defect site or loaded into a sponge/scaffold carrier and implanted. Controlled spatial delivery of cells and growth factors can be effected with self-segregating microparticles, scaffolds, and/or layered hydrogels.

As shown in FIG. 1A, the biologic compositions can be applied via various different modalities depending on the nature of the physeal injury. One modality is an injectable hydrogel comprising components 1, 2, and 3 above. Another modality is an implantable hydrogel infused scaffold comprising components 1, 2, 3 and 4 above. An injectable hydrogel can be used to treat physeal fractures and small deficits after boney tether removal, for example, and the implantable hydrogel infused scaffold can be used to treat large deficits such as those resulting from osteosarcoma resection, for example (these exemplary uses are non-limiting). In some embodiments, the injectable material can include particles, microparticles, or nanoparticles that can self-sort to discrete regions of the defect site and thereby provide spatially controlled delivery of cells, growth factors, and drugs to guide desired tissue architecture formation.

Disclosed materials and compositions can provide various different novel properties, such as the ability to control chondrogenesis by progenitor cells (e.g. mesenchymal stem cells), the ability to control progression of chondrocyte phenotype (e.g. from proliferation and matrix synthesis to terminal hypertrophy and matrix mineralization), the ability to retain/deliver growth factors and drugs, and/or the ability to support formation of gradients of key morphogens which regulate progression of chondrocyte phenotype through the epiphyseal plate zonal states, specifically, re-creating the signaling of spatial gradients in PTHrP and IHH. Some disclosed biomaterials comprise hydrogels or hydrogel impregnated scaffolds that directly modulate chondrogenesis and chondrocyte phenotype, and that support formation of endogenous or drug delivery controlled gradients in key growth factors that regulate chondrocyte phenotype. In some embodiments, microparticles or other particles secreting the biofactors PTH(1-34) (PTHrP signaling agonist, promotes maintenance of phenotype) and triiodothyronine (T3, promotes hypertrophy and IHH secretion) can produce gradients in signaling of the PTHrP and IHH pathways that can further guide progenitor cells to re-establish the zonal architecture in epiphyseal plate defects and ultimately promote normal growth of the epiphyseal plate.

Disclosed technology for physeal regeneration was tested using two models: 1) pre-assembled constructs and 2) gradient constructs. Tested pre-assembled physeal constructs were three-zoned to mimic physeal architecture using photopatterned populations of chick sternal chondrocytes (proliferative, prehypertrophic, and hypertrophic) that exhibit similar cell phenotypes to physeal chondrocytes. In experimental studies, layered fabrication was used to create constructs with the different cell populations in discrete layers. While such layered fabrication can be used therapeutically, injectable formulations can alternatively be used where the cells sort to different layers, such as by utilizing self-segregating particles as carriers.

Some investigations analyzed the effect of hydrogel composition on chondrocyte phenotype progression and hydrogel permeability to morphogens (thus intercellular signaling). The gradient constructs can comprise hMSC laden hydrogels with discrete growth factors and/or hydrogel compositions at discrete layers. The spatial delivery of growth factors coupled with hydrogel formulation can control formation of concentration gradients of the growth factors. Gradients in concentration can also be used with endogenously secreted morphogens within the pre-assembled and gradient constructs.

In some embodiments, "sensor-cells" can be incorporated in a small number into the constructs to report the local concentration of morphogens during culture in a millifluidic bioreactor. The sensor cells can be read with Förster resonance energy transfer imaging and provide a tool for functional biomaterials characterization at the microscale.

Testing has also characterized the permeability of hydrogel formulations to fluorescently labeled molecules and formation of gradients in concentration of these molecules. This technology delivers a new model to study skeletogenesis, principles to control biomolecule transport and drug delivery in instructive matrices, and methods to facilitate tissue engineering of skeletal tissue interfaces.

Disclosed technology for guiding cellular architecture formation can be applied to regenerate other spatially-stratified skeletal tissues, such as the tendon/ligament enthesis, myotendinous junction, and cartilage tide mark. Regeneration of these interfacial tissues can be needed to promote mechanical stability of tendon, ligament, and muscle transplants. The disclosed technology may also be applied to engineer other tissues with complex spatial architectures of cell phenotypes such as liver. In addition, the methodology to generate and control spatial gradients of specific morphogens can help address fundamental questions of epiphyseal plate biology, such as what is the biofactor(s) that drives chondrocyte organization into columns and orientation of their cytoskeleton.

Injectable Hydrogels

Injectable hydrogels, compared to pre-shaped scaffolds, can be more readily translated to surgical use in patients. They can be more readily infused into difficult-to-operate sites and can fill defects of variable sizes. They also accommodate the surrounding healthy tissue and induce less damage than pre-shaped scaffolds that can require tissue resection. The disclosed injectable hydrogel formulations can provide the ability to tune cell differentiation and phenotype while allowing controlled diffusion of important morphogens during growth plate regeneration. Exemplary injectable hydrogel formulations can comprise three components:

1) PEG of similar: provides mechanical stability by resisting cell mediated contraction of the hydrogel and maintains the hydrogel shape. PEG forms biocompatible and virtually bio-inert hydrogels, but is of neutral charge and relatively hydrophobic (compared to gelatin and heparin) with low electrostatic interactions with growth factors/morphogens. Alternatives include neutral hydrophilic polymers such as poly(vinyl alcohol), poly(hydroxyethyl methacrylate), poly(vinylpyrrolidone), poloxamers, and water soluble polymers with hydroxyl groups.
2) Gelatin or similar promotes cell viability compared to PEG-only gels, provides a substrate for integrin-mediated cell adhesion, and mimics the morphogen-binding properties of natural collagenous matrices. Basic morphogens can complex with gelatin via electrostatic interactions. Gelatin also provides integrin-mediated adhesion sites that are necessary for chondrocyte reorientation into growth plate columns and hypertrophic differentiation. Gelatin type A and gelatin type B can be alternatively used. Other alternatives include collagens.
3) Heparin or similar: improves growth factor retention, potentiates their signaling, and serves as an analogue of heparan sulfated glycosaminoglycans. It binds morphogens and further potentiates their signaling due to its structural similarity to heparin sulfate (HS). HS-containing proteoglycans (HSPGs) are co-receptors for over 200 proteins, and HSPGs in ECM promote IHH oligomerization. Alternatively, other polysaccharides, chondroitin sulphate, keratin sulphate, hyaluronan, alginate, chitosan and/or dextran can be used.

Hydrogels can comprise three-dimensional, hydrophilic polymeric networks capable of absorbing and retaining different amounts of water or biological fluids. The networks can be insoluble due to the presence of chemical crosslinks (e.g., junctions, tie-points) or physical crosslinks (e.g., crystallites, entanglement), which permit hydrogels to be thermodynamically compatible with water.

The hydrogel polymers can be made photochemically crosslinkable (photopolymerizable), for example by radical addition via methacrylation of the polymers and addition of a biocompatible photoinitiator, as illustrated in FIGS. 6, 8, and 9. Some materials can be made chemically crosslinkable under thiol-Michael addition (e.g. thiol-click chemistry, thiol-ene reaction) via thiol-modification of one or more of the polymer component (e.g. G or H) and methacrylation of the others. Photopolymerization can be preferred in fabricating the hydrogel infused porous scaffold device because it polymerizes rapidly (within 3 minutes), while thiol-ene crosslinking can be preferred for injectable hydrogel materials because no light is required.

In testing, the photopolymerizable hydrogels were prepared as follows. Bovine type B gelatin (MW=40,000-50,000), PEG (MW=3500-4500), and intestinal mucosa sodium heparin (MW=15,000) were methacrylated, purified, and characterized in-house. The hydrogels were prepared by dissolving polymers in HBSS, adding 0.005% w/v initiator lithium phenyl-2,4,6-trimethylbenzoyl phosphinate (LAP), and photopolymerizing with 2.5 J/cm2/mm UV-A.

Porous Scaffolds Fabricated from the Hydrogel Precursors

The porous scaffold can be made from the same polymers as the hydrogel (or other materials) and can provide structural integrity to the implantable device in large defects. Porous scaffolds can be manufactured using the hydrogel polymers (FIG. 2). They can be manufactured using freeze casting and thermal crosslinking, for example.

Hydrogel Characterization

The effects of hydrogel composition and zonal structure on chondrogenesis and chondrocyte phenotype progression were evaluated. Engineered physeal constructs designs were fabricated and tested in vivo in an orthotropic site. Additional characterizations were performed:

1) Permeability (diffusion and partition) characterization of hydrogels in vitro.
    a. We studied permeability to model fluorescent molecules and the formation of concentration gradients of these molecules in the hydrogels.
    b. We evaluated mechanical proprieties (dynamic and relaxation moduli in compression, not shown).
2) Morphogen (growth factor) effects on chondrogenesis and chondrocyte differentiation in vitro.
3) Hydrogel composition and architecture control over chondrogenesis and chondrocyte differentiation in vivo.
    a. Growth and development over time of constructs varying in hydrogel composition and construct layers, including elongation, cellular differentiation and structure, PTHrP and IHH gradients, and endochondral ossification in an in vivo murine subcutaneous implantation model.
    b. Layers contain cells at different phenotype states, growth factors, and composition.
    c. The hydrogel compositions and construct structures described will (are proposed) to generate different gradients in concentration and signaling of endogenously secreted PTHrP and IHH. We have characterized the differences in secretion of these factors by the chondrocyte populations. Their gradients in the constructs can also be visualized using sensor cells or molecular biology tools such as in situ hybridization or immuno-staining.
4) Exogenous formation of gradients in concentration and signaling of growth factors using self-segregating particles for drug delivery.
    a. The particles can be used to deliver cells, growth factors, and other chemicals in spatial domains of the construct.

Figure 4:
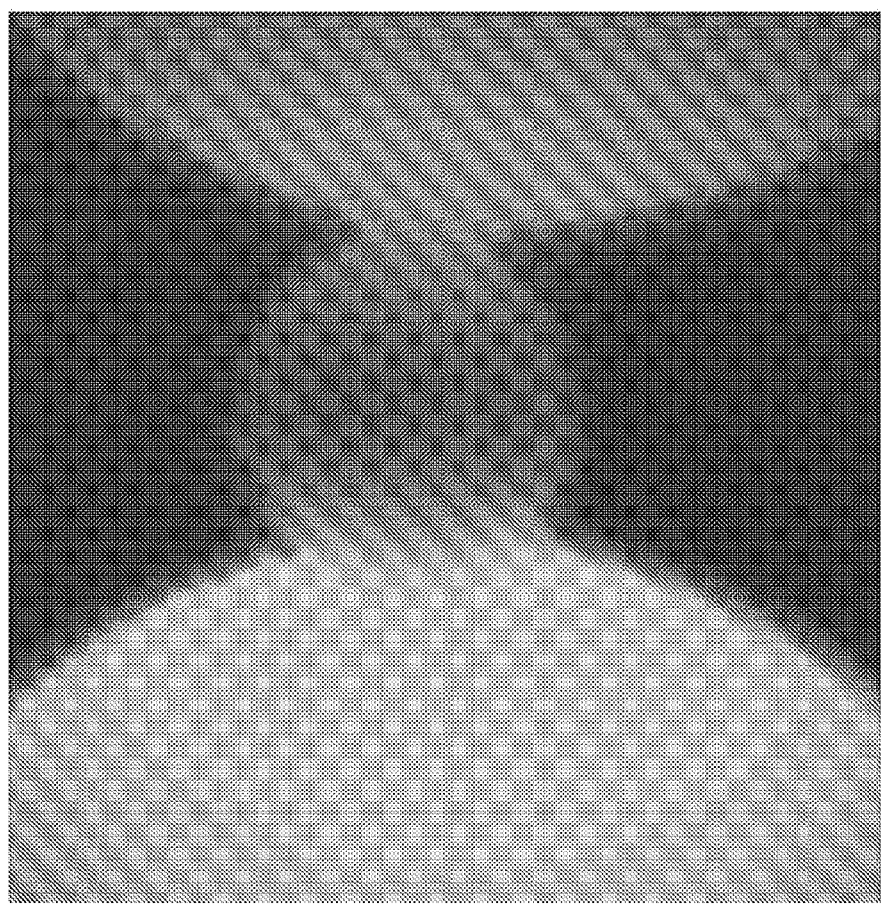
FIG. 4 shows a gradient in concentration of fluorescent dextrans of differing molecular weight across a hydrogel cylinder (center) between two medium reservoirs in a millifluidic bioreactor. Red=Dex3 3 kDa, Green=Dex10 10 kDa.

1. Permeability (Diffusion and Partition) Characterization of Hydrogels In Vitro The permeability of photocrosslinkable hydrogels can be controlled by tailoring their composition, a critical parameter to control the diffusion and binding of morphogens in the hydrogels and their gradient formation. As illustrated in FIGS. 3A-3D, permeability (Px) is a function of a molecule's (x) diffusion coefficient (Dx, transport through the hydrogel) and partition coefficient (Kx, interaction with the hydrogel). It is defined in unperfused hydrogel matrices as $Px=Kx*Dx$. In general, diffusion and partition coefficients are lower for large molecules as shown by dextrans of differing molecular weight (Dex70 & Dex10 vs. Dex3, FIG. 3C). However morphogens of smaller size but very different in polarity and hydrophilicity (Dex3 vs SFR) yielded significantly different partition coefficients (Dex3<1, SFR>1, FIG. 3C). The diffusion coefficient can be calculated in the system using the analytical solution (FIG. 3D) when the partition coefficient is 1. Increasing the fraction of gelatin and heparin in our hydrogels can decrease the diffusion coefficients but increase the partition coefficients of these morphogens. To regulate the permeability and signaling of IHH relative to PTHrP, the fractional concentration of heparin can be tailored because IHH has a high affinity for heparin and heparan sulfate proteoglycans relative to PTHrP. These hydrogels can support the formation of concentration gradients of soluble molecules between sources and sinks (FIG. 4).

Figure 5:
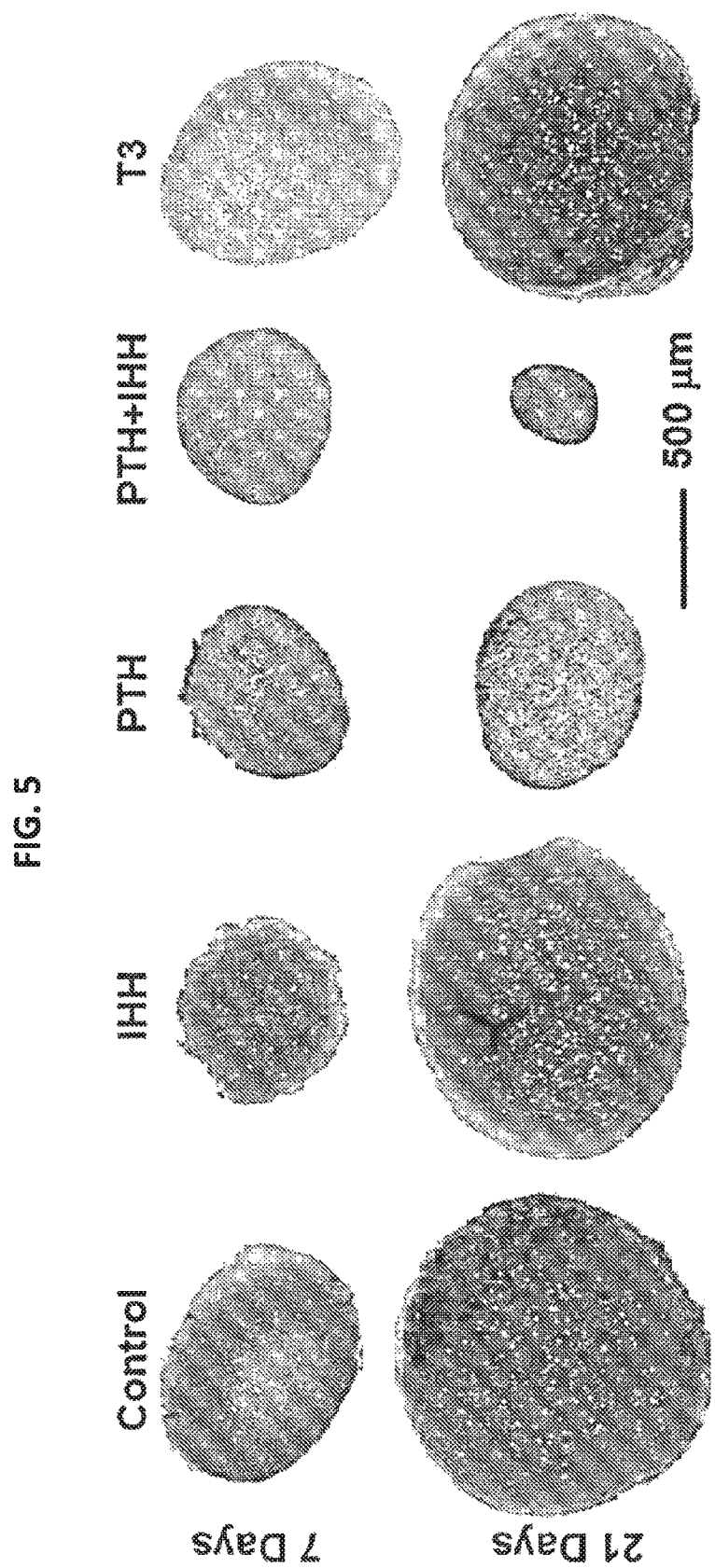
FIG. 5 shows a morphogen effect on hMSC chondrogenesis in pellet culture with chemically defined chondrogenic medium (+TGFβ-3). IHH signaling agonist (purmorphamine) treated pellets show more uniform chondrogenesis than control as evidenced by glycosaminoglycan stain (red=Safranin-O). PTH signaling agonist (PTH1-34) inhibits chondrogenesis of hMSCs compared to all other treatments. T3 (triiodothyronine) promotes hypertrophy as evidenced by larger cells at day 21. Green=fibrous tissue (fast green), Purple=cell (hematoxylin).

2. Morphogen (Growth Factor) Effects on Chondrogenesis and Chondrocyte Differentiation In Vitro The concept of using gradients to promote zonal differentiation arises from the understanding of epiphyseal plate biology and experiments that have been performed in vitro. First, it has been validated that intracellular signaling by PTHrP, IHH, and T3 pathways can control human bone marrow derived mesenchymal stem cell (hMSC) chondrogenesis and migration. In 3D cultures hMSC pellets (250, 000 cells/pellet) in chemically defined chondrogenic medium (α-MEM, 10 ng/ml TGFβ-3, ITS-X) undergo chondrogenesis over a period of 3 weeks (control group, FIG. 5). The addition of the IHH receptor agonist purmorphamine (IHH group, FIG. 5) increased chondrogenesis rate and uniformity, while addition of the PTHrP receptor agonist PTH(1-34) (PTH group. FIG. 5) suppressed chondrogenesis rate and induced matrix remodeling. Addition of both without controlling spatial delivery further inhibited chondrogenesis and led to small pellets. In 2D cultures purmorphamine increases hMSC migration while PTH(1-34) has no effect (not shown). This data, coupled with data from work with chondrocytes, shows that PTHrP prevents premature hypertrophy of chondrocytes and suggests it supports maintenance of a stem cell progenitor pool. T3 can be used to promote hypertrophy, which leads to IHH production.

Progenitor cell differentiation can be controlled in disclosed injectable hydrogels by loading the hydrogel precursor with microspheres or other small particles that secrete soluble signaling molecules which regulate formation of a gradient in PTHrP and IHH signaling in the crosslinked hydrogels. The microspheres segregate into opposing regions of the hydrogel precursor after injection. They are physically locked in place in the subsequent hydrogel crosslinking step. This establishes separate delivery locations for the morphogens and generates spatially distinct gradient fields. The IHH can diffuse to the opposite end of the defect and promote PTHrP secretion by chondrocytes, establishing the PTHrP-IHH signaling axis within hydrogel. Fluorescently dyed microparticles have been shown to segregate in tested hydrogel precursors. Similar results can occur for the delivery of PTH(1-34) and T3. In addition, layered hydrogels can be assembled with such molecules located in separate layers, such as a PTHrP analog PTH(1-34), and IHH pathway agonist purmorphamine, and T3.

3. Hydrogel Composition and Architecture Control Over Chondrogenesis and Chondrocyte Differentiation In Vivo A multiplex assay can be used to screen hydrogel compositions using a pre-assembled epiphyseal construct design (FIG. 6). Chick populations of chondrocytes were isolated at different differentiation stages (proliferative, prehypertrophic, and hypertrophic). It was verified that cells differed in phenotype as evidence by immunohistochemical staining of sterna (source) for collagen type II versus. X, and in production of the key physeal morphogens PTHrP and IHH using ELISA (not shown). These populations were assembled in 3 distinct layers (zones) of about equal thickness in cylindrical hydrogel constructs (10% w/v, 5 mm diameter×3 mm thickness, 30 million/mL) using layered photo-assembly with the prehypertrophic layer sandwiched between the proliferative, and hypertrophic layers. They were implanted in dorsal subcutaneous pockets of 8 week old immuno-compromised male mice. Mice were sacrificed at 1, 3, and 8 weeks and the implants were removed for histology (e.g. GAG staining) and immunohistochemistry evaluation (e.g. collagen type II and X).

These cells and constructs were used to evaluate the effects of two hydrogel formulations, methacrylated gelatin (G Hydrogel, 10% w/v) and a composite (PGH Hydrogel, 10% w/v) of G with methacrylated poly(ethylene glycol) (PEG) and methacrylated heparin, on micro-tissue growth in-vitro and in-vivo. Proliferative chondrocytes normally produce high amounts of collagen type H and glycosaminoglycan (GAG) extracellular matrix (ECM) while hypertrophic chondrocytes express high levels of collagen type X and go on to mineralize the ECM. The addition of heparin to the PGH hydrogel (formulation 6.3% P, 2.1% G, and 1.6% H w/v) augments maintenance of proliferative chondrocytes in glycosaminoglycan producing state (FIG. 6A) and delays development of the hypertrophic phenotype which was most apparent at 3 weeks (FIGS. 6C, 6E). However, the G hydrogel (same total density=10% w/v) leads to decreased GAG synthesis (FIG. 6B) and accelerated hypertrophy (FIG. 6F) and ECM mineralization (FIG. 6D). Cell stacking was observed, but not longitudinally oriented along the cylinder axis. The G constructs showed a non-uniform GAG stain with the intensity lessening away from the proliferative layer and near the cylinder wall. The gradient of GAG staining in G constructs (top to bottom) may indicate that a diffusing biofactor from the proliferative layer impacts GAG production in the neighboring layers. The PGH scaffold may have greater retention of this factor due to heparin incorporation leading to a more uniform stain in the hypertrophic zones (Z3, Z4). These cartilaginous constructs grow well in the subcutaneous implant site, a compartment of low vascularity compared to bone sites. They also promote local angiogenesis surrounding the neotissue. These results show that selecting biomaterials, which support the physeal chondrocyte phenotypes and signaling across zones, is essential to promote establishment of physeal-like structure (e.g. oriented columnar stacking).

Evaluation of hydrogel composition effects on chondrogenic differentiation by human MSCs was performed using the same two hydrogel formulations, subcutaneous implantation model, and experimental time-points. Assembled cylindrical hydrogel constructs had the same dimensions as above (10% w/v, 5 mm diameter×3 mm thickness) with the hMSCs uniformly seeded throughout at 30 million/mL. However here the layered photo-assembly was used to pattern the growth factors to discrete layers of the scaffold with the goal of controlling the chondrocyte differentiation into tonal states similar to the epiphyseal growth plate, subsequent to the initial chondrogenic differentiation by the MSCs (FIG. 7). The growth factors were carried in the hydrogel proper and expected to have a rapid release lasting less than a week. Microparticles were not used for the growth factor delivery. The same hydrogel formulations were used, G and PGH (FIG. 7, 1st vs. 2nd rows). The hMSCs were encapsulated in the hydrogel as either individual cells or cellular microclusters (FIG. 7, left vs. right side). The microclusters were used to test the effectiveness of cell-cell contact in promoting chondrogenesis of hMSCs. Contact mediated signaling via cadherins modulates the initial commitment of MSCs to the chondrogenic lineage. The ability of the hydrogels alone, sans spatial delivery of the growth factors, was also tested to promote zonal states of chondrocyte differentiation (FIG. 7, bottom row).

In general, the PGH hydrogel maintained the "stemness" of hMSCs longer and shows no fibrous or osteoblastic differentiation, only chondrogenic staining (FIG. 8). In contrast the G hydrogel promotes both osteogenesis and chondrogenesis throughout the construct as evidenced by both fibrous tissue and cartilaginous tissue staining, and mineralization concomitant with the fibrous tissue (FIG. 9). Thus the PGH hydrogel is suitable for physeal plate regeneration as the direct osteogenesis by hMCSs in the G hydrogel is undesirable for the expansive growth that must take place. However, the composite constructs composed of both G and PGH as in the lower row of FIG. 7 may be used to engineer tissue interfaces that do not demonstrate spatial growth such as the enthesis and tide mark.

4) Exogenous Formation of Gradients in Concentration and Signaling of Growth Factors Using Self-Segregating Microparticles for Drug Delivery.

Self-segregating particles (e.g., microparticles, nanoparticles, etc.), can be configured to be carried in the injectable hydrogel precursors and segregate prior to hydrogel cross-linking. In some embodiments, the particles separate based on density separation in a gravitational filed. The particles can comprise alginate microbeads and alginate coatings of nanoparticles and microparticles that adjust particle density to greater of less than the hydrogel. Heavier particles can be made by using high alginate density and/or ionic crosslinking while lighter particles can be made by incorporation of a salt that produces gas, for example calcium carbonate and activation in a mild glucuronic acid solution which does not adversely affect cell viability or growth factor activity. The injury site can be positioned so that the desired axis of particle segregation is aligned perpendicular to the ground (along earth's gravitational field). Injection of the particle laden hydrogel into a defect causes the particles to self-sort to opposite regions of the defect site and thereby provide spatially controlled delivery of cells, growth factors, and drugs to guide proper tissue architecture formation. Alternative particle materials include coacervates (e.g. heparin with PEAD), and alpha hydroxy acids. Any particles can be used that provide a range of densities that spans across the density of the medium material in which the particles are present. Alternatively, other sorting mechanisms can be used, such as magnetic sorting based a range magnetic responses within a varied magnetic field that is applied (e.g., via MRI).

Additional Features and Embodiments

Disclosed regeneration technology provides many beneficial innovations in the application of biomaterials that re-create gradients of key morphogens which regulate chondrocyte differentiation through the epiphyseal plate zonal states. For example, we have developed a novel morphogen delivery system where drug carriers self-segregate to different regions of the defect. The materials can also be pre-patterned to contain the growth factors in different regions of an implant. In addition, specifically tailored hydrogel matrix formulations can control the diffusion and matrix binding (e.g. the permeability) of the delivered morphogens, and thereby the gradient that they form in the defect can be carefully controlled. Furthermore, disclosed hydrogel formulations can promote chondrogenesis of MCS without osteogenesis. The disclosed technology can be used to repair large defects resulting from resection of diseased epiphyseal plate tissue by using photopolymerization to fabricate large monolithic constructs that can be implanted. The disclosed approaches to guide cellular architecture formation can also be applied to regenerate other spatially-stratified skeletal tissues like the tendon/ligament enthesis, myotendinous junction, and cartilage tide mark. Regeneration of these interfacial tissues is needed to promote mechanical stability of tendon, ligament, and muscle transplants. The disclosed technology can also be applied to repair articular cartilage defects caused by arthritis and traumatic injury, for example.

Figure 10:
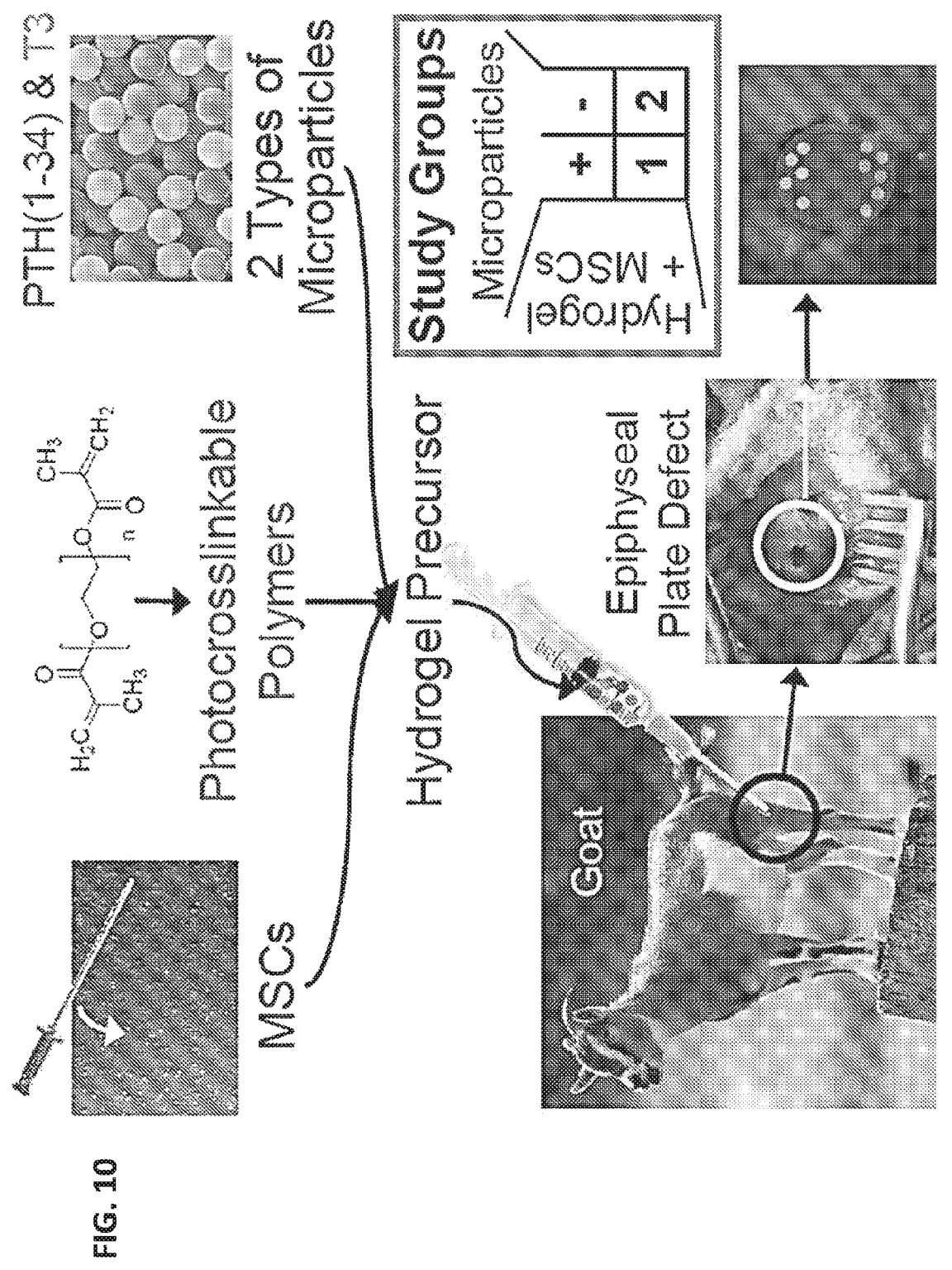

A preclinical test of the disclosed technology has also been conducted for regenerating epiphyseal plate damage. The disclosed approach is tested in cylindrical defects (15 mm deep×3.2 mm diameter) made in the proximal tibia epiphyseal plate of immature 3 month old goats (FIG. 10). This large model animal is helpful because it more accurately replicates the defect sizes, mechanical forces and vascular environment of human injury than small model animals or in vitro experiments. It more closely replicates human injury and repair, including the spatial domain in which the morphogens act. Thus it is a more rigorous test of the disclosed therapeutic approaches. This large model animal study investigates the utility of the PGH hydrogel in inhibiting boney tether formation growth disruption, and the utility of stem cells in restoring growth, using the following groups:

1. Unoperated controls to quantify normal growth
2. Empty defect control
3. Defect filled with PGH hydrogel delivering TGFs via hydrogel and nanoparticles (uniform spatial distribution)
4. Defect filled with PGH hydrogel containing TGFs and goat MSCs A fifth group was also added to test the efficacy of immunomodulation in preventing tether formation and facilitating epiphyseal repair. Subsequently, we test the benefit of controlled spatial delivery of microparticles delivering growth factors that modulate the phenotype progression of neo-chondrocytes within the defect as in FIG. 10.

Additional Applications, Test Data, and Future Studies

The disclosed biomaterials, constructs, and other disclosed technology continues to be evaluated for regeneration of bone, cartilage, and the physis using in vitro and in vivo experiments. The following are examples of recent and/or current studies:

1. We are testing how the individual components of the PGH hydrogel impact stem cell differentiation and chondrocyte phenotype progression using in vitro experiments with human stem cells and chick chondrocyte cells, respectively. We have first added inhibitors of specific cell signaling pathways to determine if the inhibition of mineralization in the PGH hydrogel is due to differences in hydrogel stiffness or signaling of collagen degradation products. We further plan to determine how the hydrogel modulates differentiation and phenotype progression (with the goal to create optimum hydrogel formulations) by 1) creating hydrogels with one (or more) of the PGH hydrogel polymeric components removed, and 2) creating hydrogels of different density (% w/v).
2. We are awaiting histological results for 8 goats we operated on in February 2016 testing physeal regeneration in a goat model (samples harvested in June 2016). This model tests re-formation of the gradient tissue architecture of the physis using the PGH hydrogel (10% w/v) laden with allogenic stem cells (30×106/ml) and coacervate nanoparticles delivery of ±TGF-β1 & TGF-β3 (to drive chondrogenesis, note TGF-β3 not in coacervates but doped into gel) and ±IL-10 (to suppress deleterious immune response to non-autogenous cells and surgery).
3. We are currently testing physeal regeneration in a second round of the goat model. This model test re-formation of the gradient tissue architecture using the PGH hydrogel and spatially discrete delivery of growth factors with the self-segregating microparticles. We operated 8 goats in December 2016 and will harvest tissues in March 2017. The hydrogels were PGH (8% w/v) laded with autologous stem cells (30×106/ml). Note: 1) the decrease in hydrogel density to better promote cell viability and chondrogenesis, 2) use of autologous cells (cells isolated and implanted into same goat). We used TGF-β1 to promote chondrogenesis, T3 to promote hypertrophy, and PTH(1-34) to maintain a reserve cell pool (maintain stem cell "sternness"). These drugs were delivered via coacervate nanoparticles. The 4 groups were: 1) empty defect, 2) hydrogel with only TGF-β1 throughout, 3) tri-layered hydrogel made with TGF-β1 throughout but T3 in bottom layer and PTH in top layer, and 4) tri-layered made with TGF-β1 throughout but T3 in bottom layer via delivery in microparticles that sink and PTH in top layer via microparticles that float. The microparticles were made as described in the disclosure, with the drugs carried by coacervate microparticles embedded within the microparticles.

4. We have begun planned research evaluating the PGH hydrogel for bone regeneration via endochondral ossification in a porcine model of both 1) segmental bone defect and 2) comminuted fracture. This study is expected to span the next 3 years and includes 9 treatment groups in 45 animals. It evaluates the PGH hydrogel with/without stem cells and delivery of TGF-β1 and IL-10 for chondrogenic and immunomodulatory purposes.

5. Planned research will further evaluate chondrogenesis by human stem cells in a murine subcutaneous model. For example, we will test the PGH hydrogel at lower densities (e.g. 8%).

6. Planned research will include optimizing microparticle fabrication using silicone oil instead of organic oils (e.g., olive oil). In the future we may use a microfluidic system to control polydispersity of microparticle size.

Figure 11:
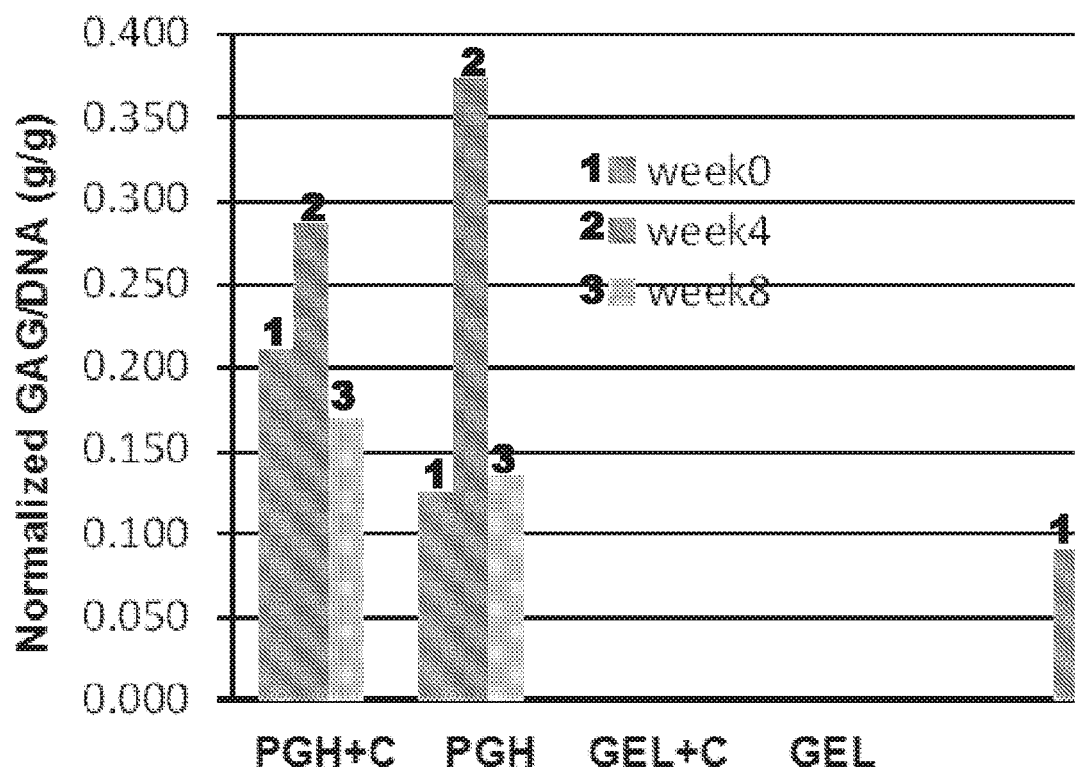
FIG. 11 is a graph showing normalized GAG/DNA values for different test materials over time.
Figure 12:
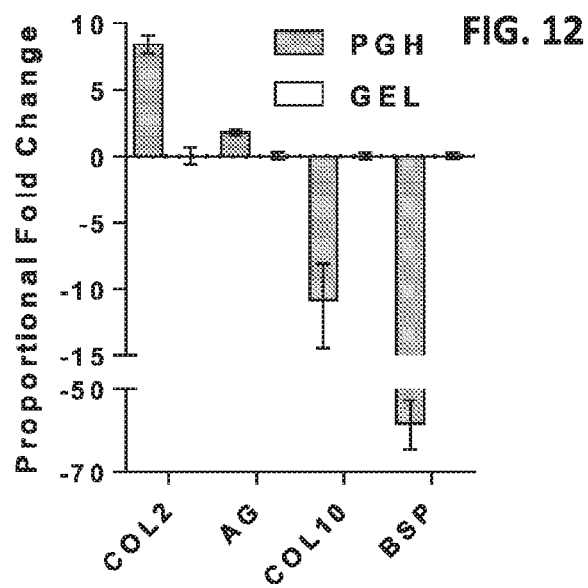
FIG. 12 is a graph showing proportional fold change for PGH and GEL for different test materials.

FIGS. 11 and 12 illustrate test data that shows quantitatively that the disclosed PGH hydrogels promote chondrogenesis over osteogenesis compared to the GEL hydrogel. This data is for 10% w/v hydrogels (5 mm diameter×3 mm height) seeded with human stem cells ($3\times10^6$/ml) after 8 weeks subcutaneous culture in mice. +C indicates cells were pre-clustered before encapsulation in hydrogels. FIG. 11 shows measurement of glycosaminoglycan (GAG) composition in hydrogel. Both PGH groups indicate chondrogenesis by GAG content. FIG. 12 shows that Col2 and AG are markers of chondrogenesis, higher in the PGH. Col10 and BSP are makers of chondrocyte hypertrophy and osteogenesis, lower in the PGH.

FIGS. 13 and 14 illustrate additional test data determining how the PGH hydrogel composition affects chondrocyte phenotype progression. This data is for PGH hydrogel (10% w/v) by embryonic day 17 chicken sternal chondrocytes ($3\times10^6$/ml) of different phenotype (i.e., proliferative, pre-hypertrophic, hypertrophic) after 8 weeks subcutaneous growth in mice. In FIG. 13, the top row shows GAG staining in the hydrogel (proliferative chondrocytes produce more). Note that the pre-hypertrophic and hypertrophic cells also produce GAG, though they are also staining positive for collagen type 10 (Col-10), as shown in the bottom row of FIG. 13. We now know that the PGH hydrogel permits hypertrophic differentiation at a rate likely delayed to normal development in vivo (in the animal) and that PGH effectively inhibits terminal differentiation (mineralization and death). Instead PGH keeps the hypertrophic cells in a GAG producing state. The GEL hydrogel shows mineralization at rates consistent with in vivo growth of the sternum. We have 1, 3 and 8 week time course images showing development of Col-10 expression in the different populations. FIG. 14 quantifies that the PGH hydrogel help maintains chondrogenic phenotype (GAG production) of individual chondrocytes even though they are hypertrophic (expressing Col-10).

Figure 15:
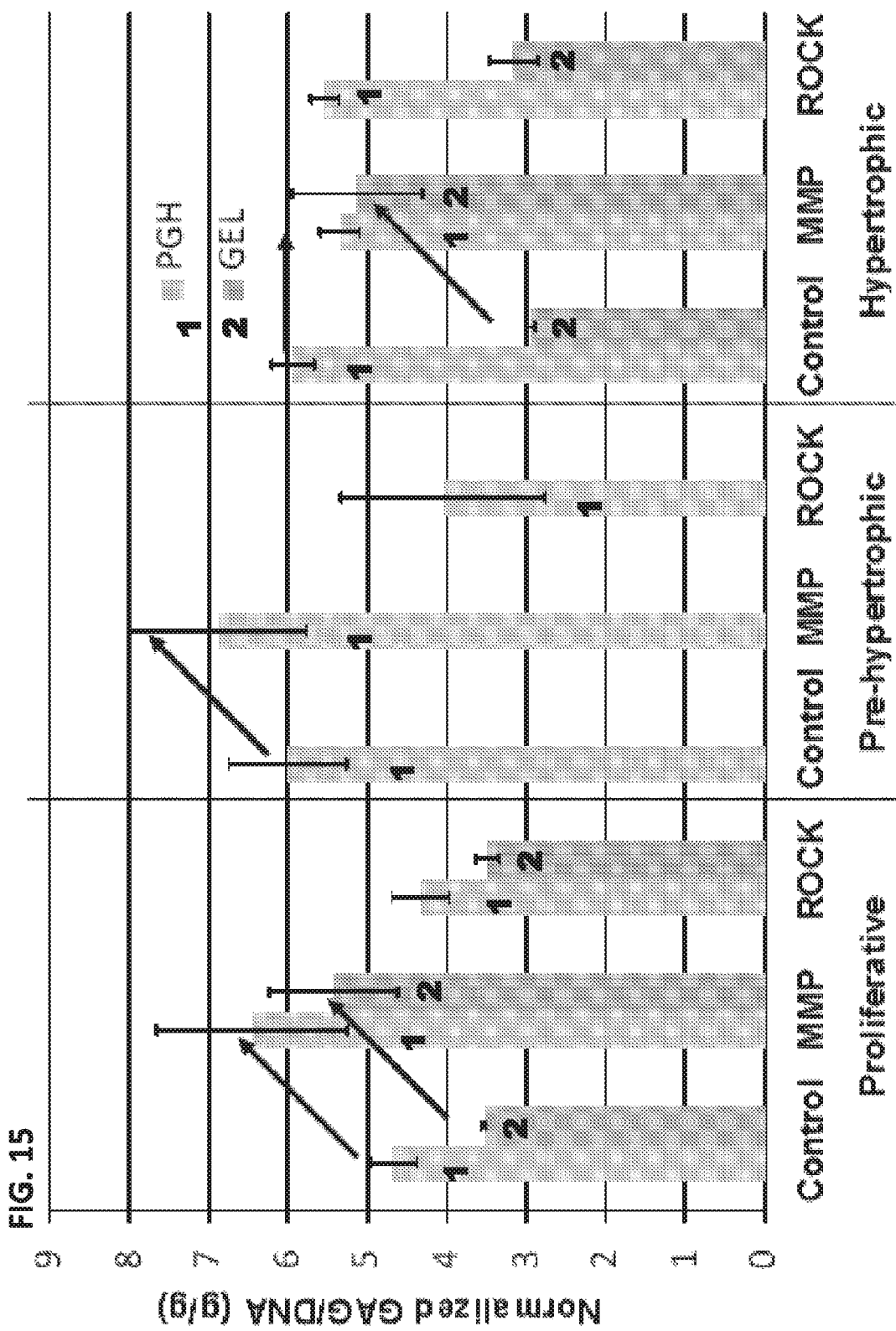
FIG. 15 is a graph illustrating normalized GAG/NDA value differences between control, MMP, and ROCK, for proliferative, pre-hypertrophic, and hypertrophic examples.

Additional test data shows that the effect of PGH on chondrogenesis might be due to the decreased collagen signaling (due to lower gelatin content). We tested 10% w/v hydrogels laded with $3\times10^6$/ml of the 3 different chick chondrocyte populations, but cultured in vitro for 1 week (as opposed to in vivo in the subcutaneous model). FIG. 15 shows that inhibition of matrix metalloproteinases (MMPs) using GM6001 (MMP labeled group) increased GAG accumulation in both PGH and GEL hydrogels. This suggests that more cells are retained in a chondrogenic state (progression to hypertrophy delayed) when signaling by collagen degradation fragments is reduced by MMP inhibition. Inhibition of ROCK signaling with Y27362 (ROCK labeled group) did not change GAG levels, suggesting that any potential difference in matrix stiffness between hydrogels is not responsible for the differences in GAG accumulation. Furthermore, ROCK results suggests that hydrogels stiffness and/or cell adhesion is/are not promoting phenotype progression (hydrogel is not too stiff/cells are not adhering so strongly to develop actin stress fibers). It is believed that the MMP inhibitor decreases mineralization and that the collagen fragment components are driving in part phenotype progression.

Self-segregating microparticles has also been developed and are currently being tested for their biological efficacy with goats.

Overall, the results disclosed herein support the PGH hydrogel as a promising material for physeal engineering because it supports endochondral ossification while inhibiting direct osteogenesis by progenitor cells, and because it still supports progression of chondrocytes through their differentiation states. The results also show that the PGH hydrogel is ideal for cartilage regeneration because it inhibits direct osteogenesis by stem cells and inhibits cell mineralization of the matrix.

Further ongoing studies regarding this technology include development of the technology for physeal regeneration in children and for bone regeneration in compromised wounds.

For physeal regeneration applications, ongoing research includes the above-described goat-based study (8 goats). Future steps include a larger (more animals) pre-clinical test/optimization of the technology (e.g., test three hydrogel densities, fine-tuning of relative ratios of polymer components, high/low dosing of drugs) to promote fast chondrogenesis, formation of physeal architecture, and demonstrate continued physeal growth. The current goat study will address some of these issues, namely that the microparticles can control spatial delivery of growth factors to induce physeal architecture formation.

For bone regeneration applications, planned research includes a large pre-clinical study in pigs that tests/optimizes hydrogel drug dosing for chondrogenesis and remodeling into bone.

For temporomandibular joint (TMJ) condyle regeneration applications, planned research includes a pilot study of using the disclosed hydrogel technology as one component of a composite device to regenerate the mandibular condyle. An exemplary device is composed of two layers: 1) top of PGH to promote chondrogenesis, 2) bottom of GEL to promote direct osteogenesis by stem cells, with a resorbable magnesium mesh at the base of the bottom layer to provide mechanical integrity for insertion.

For cartilage regeneration applications, future studies may include a study in an osteochondral defect of the knee using an approach similar to the TMJ condyle project described in the previous paragraph.

A significant applicant of the disclosed hydrogel-based technology is as articular cartilage resurfacing and focal defect filling material. Additional fields of application may include any application of regenerative medicine where tissues with gradient structures must be repaired; e.g., tendon ligament enthesis (insertion site into bone).

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B. and/or C" means "A", "B.", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A biomaterial comprising:
   a hydrogel precursor capable of carrying growth factors and mesenchymal stem cells (MSCs);
   chondrogenic and immunomodulatory cytokines; and
   self-segregating particles capable of prolonged and spatially controlled growth factor delivery, wherein the self-segregating particles are distinct from molecules of the hydrogel precursor and segregate to different positions within the hydrogel precursor;
   wherein the biomaterial is injectable for regeneration of an epiphyseal growth plate.

2. The biomaterial of claim 1, wherein the hydrogel precursor comprises PEG, gelatin, and heparin.

3. The biomaterial of claim 1, wherein the self-segregating particles vary in density and self-segregate relative to the hydrogel precursor based on gravity.

4. The biomaterial of claim 1, wherein the biomaterial can control chondrogenesis by progenitor cells.

5. The biomaterial of claim 1, wherein the biomaterial can control progression of chondrocyte phenotype.

6. The biomaterial of claim 1, wherein the biomaterial can retain and deliver growth factors and drugs.

7. The biomaterial of claim 1, wherein the biomaterial can support formation of gradients of key morphogens which regulate progression of chondrocyte phenotype through the epiphyseal plate zonal states, specifically, recreating the signaling of spatial gradients in PTHrP and IHH.

8. An implantable hydrogel infused scaffold for regeneration of an epiphyseal growth plate, comprising:
   a porous scaffold providing mechanical support;
   a hydrogel carrying growth factors and mesenchymal stem cells (MSCs);
   chondrogenic and immunomodulatory cytokines; and
   self-segregating particles for prolonged and spatially controlled growth factor delivery wherein the self-segregating particles are distinct from molecules of the hydrogel and are segregated within the hydrogel.

9. The implantable hydrogel infused scaffold of claim 8, wherein the hydrogel comprises PEG, gelatin, and heparin.

10. The implantable hydrogel infused scaffold of claim 8, wherein the self-segregating particles vary in density and self-segregate relative to the hydrogel based on gravity.

11. The implantable hydrogel infused scaffold of claim 8, wherein the implantable hydrogel infused scaffold can control chondrogenesis by progenitor cells.

12. The implantable hydrogel infused scaffold of claim 8, wherein the implantable hydrogel infused scaffold can control progression of chondrocyte phenotype, including from proliferation and matrix synthesis to terminal hypertrophy and matrix mineralization.

13. The implantable hydrogel infused scaffold of claim 8, wherein the implantable hydrogel infused scaffold can retain and deliver growth factors and drugs.

14. The implantable hydrogel infused scaffold of claim 8, wherein the implantable hydrogel infused scaffold can support formation of gradients of key morphogens which regulate progression of chondrocyte phenotype through the epiphyseal plate zonal states, specifically, recreating the signaling of spatial gradients in PTHrP and IHH.

* * * * *